(12) United States Patent
Lehtinen et al.

(10) Patent No.: US 10,093,946 B2
(45) Date of Patent: Oct. 9, 2018

(54) AXMI477, AXMI482, AXMI486 AND AXMI525 TOXIN GENES AND METHODS FOR THEIR USE

(71) Applicant: Athenix Corp., Morrisville, NC (US)

(72) Inventors: Duane Alan Lehtinen, Cary, NC (US); Kimberly S. Sampson, Durham, NC (US); Kira Roberts, Bahama, NC (US); Ethan Dunn, Durham, NC (US)

(73) Assignee: BASF SE, Ludwigshafen (DE)

( * ) Notice: Subject to any disclaimer, the term of this patent is extended or adjusted under 35 U.S.C. 154(b) by 15 days.

(21) Appl. No.: 15/102,785

(22) PCT Filed: Dec. 8, 2014

(86) PCT No.: PCT/US2014/068989
§ 371 (c)(1),
(2) Date: Jun. 8, 2016

(87) PCT Pub. No.: WO2015/088937
PCT Pub. Date: Jun. 18, 2015

(65) Prior Publication Data
US 2016/0311865 A1 Oct. 27, 2016

Related U.S. Application Data

(60) Provisional application No. 61/913,905, filed on Dec. 9, 2013, provisional application No. 61/913,911, filed on Dec. 9, 2013.

(51) Int. Cl.
*C07K 14/325* (2006.01)
*C12N 15/82* (2006.01)

(52) U.S. Cl.
CPC ........ *C12N 15/8286* (2013.01); *C07K 14/325* (2013.01); *Y02A 40/162* (2018.01)

(58) Field of Classification Search
None
See application file for complete search history.

(56) References Cited

U.S. PATENT DOCUMENTS

| | | | |
|---|---|---|---|
| 9,000,261 B2 * | 4/2015 | Abad | C07K 14/32 800/279 |
| 2010/0298207 A1 * | 11/2010 | Sampson | A01N 63/02 514/2.4 |

OTHER PUBLICATIONS

Palma et al, 2014, Toxins 6:3296-3325.*
Argolo-Filho et al, 2014, Insects 5:62-9.*

* cited by examiner

*Primary Examiner* — Anne R Kubelik

(57) ABSTRACT

Compositions and methods for conferring pesticidal activity to bacteria, plants, plant cells, tissues and seeds are provided. Compositions comprising a coding sequence for a *Bacillus thuringiensis* toxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated toxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:5-26, or the nucleotide sequence set forth in SEQ ID NO: 1-4, as well as variants and fragments thereof.

24 Claims, No Drawings
Specification includes a Sequence Listing.

AXMI477, AXMI482, AXMI486 AND AXMI525 TOXIN GENES AND METHODS FOR THEIR USE

CROSS REFERENCE TO RELATED APPLICATIONS

This application claims the benefit of U.S. Provisional Application Ser. No. 61/913,905, filed Dec. 9, 2013, and U.S. Provisional Application Ser. No. 61/913,911, filed Dec. 9, 2013, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA136054 ST25.txt", created on Nov. 14, 2014, and having a size of 97 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Hemipteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A nomenclature was described for the Cry genes based upon amino acid sequence homology rather than insect target specificity (Crickmore et al. (1998) *Microbiol. Mol. Biol. Rev.* 62:807-813). In this classification, each toxin is assigned a unique name incorporating a primary rank (an Arabic number), a secondary rank (an uppercase letter), a tertiary rank (a lowercase letter), and a quaternary rank (another Arabic number). Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer, and the improvement in yield by controlling insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise bacteria, plants, plant cells, tissues, and seeds comprising the nucleotide sequence of the invention.

In particular, isolated or recombinant nucleic acid molecules are provided that encode a pesticidal protein. Additionally, amino acid sequences corresponding to the pesticidal protein are encompassed. In particular, the present invention provides for an isolated or recombinant nucleic acid molecule comprising a nucleotide sequence encoding the amino acid sequence shown in SEQ ID NO:5-26 or a nucleotide sequence set forth in SEQ ID NO:1-4, as well as biologically-active variants and fragments thereof. Nucleotide sequences that are complementary to a nucleotide sequence of the invention, or that hybridize to a sequence of the invention or a complement thereof are also encompassed. Further provided are vectors, host cells, plants, and seeds comprising the nucleotide sequences of the invention, or nucleotide sequences encoding the amino acid sequences of the invention, as well as biologically-active variants and fragments thereof.

Methods are provided for producing the polypeptides of the invention, and for using those polypeptides for controlling or killing a lepidopteran, hemipteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling, for example, with members of the Cry1, Cry2, and Cry9 families of endotoxins. The proteins find use in controlling or killing lepidopteran, hemipteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, Hemiptera and Coleoptera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Thus, provided herein are novel isolated or recombinant nucleotide sequences that confer pesticidal activity. These nucleotide sequences encode polypeptides with homology to known delta-endotoxins or binary toxins. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. Also encompassed herein are nucleotide sequences capable of hybridizing to the nucleotide sequences of the invention under stringent conditions as defined elsewhere herein. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "recombinant" nucleic acid sequence (or DNA) is used herein to refer to a nucleic acid sequence (or DNA) that is no longer in its natural environment, for example in an in vitro or in a recombinant bacterial or plant host cell. In some embodiments, an isolated or recombinant nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1-4, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the pesticidal proteins encoded by these nucleotide sequences are set forth in SEQ ID NO:5-26.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. Thus, biologically-active fragments of the polypeptides disclosed herein are also encompassed. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. In another embodiment, the pesticidal activity is hemiptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050 contiguous amino acids, or up to the total number of amino acids present in a full-length pesticidal protein of the invention. In some embodiments, the fragment is a proteolytic cleavage fragment. For example, the proteolytic cleavage fragment may have an N-terminal or a C-terminal truncation of at least about 30 amino acids, at least about 40 amino acids, at least about 50, at least about 100 amino acids, about 120, about 130, about 140, about 150, about 160, about 170, about 180, about 190, about 200, about 210, about 220, about 230, about 240, about 250, about 275, about 300, about 350, about 400, about 450, about 500, or about 550 amino acids relative to SEQ ID NO:2, 3, 4, 5, 6, or 7. In some embodiments, the fragments encompassed herein result from the removal of the C-terminal crystallization domain, e.g., by proteolysis, or by insertion of a stop codon in the coding sequence. In some embodiments, the fragments encompassed herein result from the removal of the N-terminal signal peptide. N-terminal truncations may further comprise a methionine residue at the N-terminus.

Preferred pesticidal proteins of the present invention are encoded by a nucleotide sequence sufficiently identical to the nucleotide sequence of SEQ ID NO:1-4, or the pesticidal proteins are sufficiently identical to the amino acid sequence set forth in SEQ ID NO:5-26. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1-26). The percent identity between two sequences can be determined using techniques similar to those described below, with or without allowing gaps. In calculating percent identity, typically exact matches are counted. A gap, i.e. a position in an alignment where a residue is present in one sequence but not in the other, is regarded as a position with non-identical residues.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) Trends Genetics 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Thus, the present invention encompasses probes for hybridization, as well as nucleotide sequences capable of hybridization to all or a portion of a nucleotide sequence of the invention (e.g., at least about 300 nucleotides, at least about 400, at least about 500, 1000, 1200, 1500, 2000, 2500, 3000, 3500, or up to the full length of a nucleotide sequence disclosed herein). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in SEQ ID NO:5-26. Fragments, biologically active portions, and variants thereof are also provided, and may be used to practice the methods of the present invention. An "isolated protein" or a "recombinant protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in SEQ ID NO:5-26, and that exhibit pesticidal activity. A biologically active portion of a pesticidal protein can be a polypeptide that is, for example, 10, 25, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.*

83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:5-26. The invention encompasses other fragments, however, such as any fragment in the protein greater than about 10, 20, 30, 50, 100, 150, 200, 250, 300, 350, 400, 450, 500, 550, 600, 650, 700, 750, 800, 850, 900, 950, 1000, 1050, 1100, 1150, 1200, 1250, 1300, 1350 or more amino acids in length.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:5-26. Variants also include polypeptides encoded by a nucleic acid molecule that hybridizes to the nucleic acid molecule of SEQ ID NO:1-4, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

In various embodiments of the present invention, pesticidal proteins include amino acid sequences deduced from the full-length nucleotide sequences disclosed herein, and amino acid sequences that are shorter than the full-length sequences due to the use of an alternate downstream start site. Thus, the nucleotide sequence of the invention and/or vectors, host cells, and plants comprising the nucleotide sequence of the invention (and methods of making and using the nucleotide sequence of the invention) may comprise a nucleotide sequence encoding an amino acid sequence corresponding to SEQ ID NO:6, 7, 8, 9, 10, 12, 13, 14, 16, 17, 18, 19, 21, 22, 23, 24, 25 and 26.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Thus, one aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NO:5-26 or a fragment thereof. In another embodiment, the antibody specifically binds to a fusion protein comprising an amino acid sequence selected from the amino acid sequence set forth in SEQ ID NO:5-26 or a fragment thereof.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

The antibodies of the invention may be contained within a kit useful for detection of the protein or peptide molecules of the invention. The invention further comprises a method of detecting the protein or peptide molecule of the invention (particularly a protein encoded by the amino acid sequence set forth in SEQ ID NO:5-26, including variants or fragments thereof that are capable of specifically binding to the antibody of the invention) comprising contacting a sample with the antibody of the invention and determining whether the sample contains the protein or peptide molecule of the invention. Methods for utilizing antibodies for the detection of a protein or peptide of interest are known in the art.

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:5-26, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a nonmutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A pesticidal sequence of the invention may be provided in an expression cassette for expression in a plant of interest.

By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and/or 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

In various embodiments, the nucleotide sequence of the invention is operably linked to a promoter, e.g., a plant promoter. "Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, U.S. Patent Publication No. 20090137409, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In various embodiments, the transgenic plant further comprises one or more additional genes for insect resistance (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families; etc.). It will be understood by one of skill in the art that the transgenic plant may comprise any gene imparting an agronomic trait of interest.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from Agrobacterium to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing strains comprising a nucleotide sequence of the present invention, or a variant thereof, in pest control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene of the invention and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of the target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application.

The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, hemipteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, the crystal and/or the spore suspension, or the isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Hemipteran pests (which include species that are designated as Hemiptera, Homoptera, or Heteroptera) include, but are not limited to, *Lygus* spp., such as Western tarnished plant bug (*Lygus hesperus*), the tarnished plant bug (*Lygus lineolaris*), and green plant bug (*Lygus elisus*); aphids, such as the green peach aphid (*Myzus persicae*), cotton aphid (*Aphis gossypii*), cherry aphid or black cherry aphid (*Myzus cerasi*), soybean aphid (*Aphis glycines* Matsumura); brown plant hopper (*Nilaparvata lugens*), and rice green leafhopper (*Nephotettix* spp.); and stink bugs, such as green stink bug (*Acrosternum hilare*), brown marmorated stink bug (*Halyomorpha halys*), southern green stink bug (*Nezara viridula*), rice stink bug (*Oebalus pugnax*), forest bug (*Pentatoma rufipes*), European stink bug (*Rhaphigaster nebulosa*), and the shield bug *Troilus luridus*.

Insect pests of the invention for the major crops include: Maize: *Ostrinia nubilalis*, European corn borer; *Agrotis ipsilon*, black cutworm; *Helicoverpa zea*, corn earworm;

*Spodoptera frugiperda*, fall armyworm; *Diatraea grandiosella*, southwestern corn borer; *Elasmopalpus lignosellus*, lesser cornstalk borer; *Diatraea saccharalis*, sugarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctate*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid; Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin; Cereals Herbicides: 2.4-D, Amidosulfuron, Bromoxynil, Carfentrazone-E, Chlorotoluron, Chlorsulfuron, Clodinafop-P, Clopyralid, Dicamba, Diclofop-M, Diflufenican, Fenoxaprop, Florasulam, Flucarbazone-NA, Flufenacet, Flupyrosulfuron-M, Fluroxypyr, Flurtamone, Glyphosate, Iodosulfuron, Ioxynil, Isoproturon, MCPA, Mesosulfuron, Metsulfuron, Pendimethalin, Pinoxaden, Propoxycarbazone, Prosulfocarb, Pyroxsulam, Sulfosulfuron, Thifensulfuron, Tralkoxydim, Triasulfuron, Tribenuron, Trifluralin, Tritosulfuron; Cereals Fungicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluopyram, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin; Cereals Insecticides: Dimethoate, Lambda-cyhalthrin, Deltamethrin, alpha-Cypermethrin, ß-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, ß-Cyfluthrin, Cypermethrin, Bifenthrin, Lufenuron, Tebupirimphos, Ethiprole, Cyazypyr, Thiacloprid, Acetamiprid, Dinetofuran, Avermectin; Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Etofenprox, Carbofuran, Benfuracarb, Sulfoxaflor; Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, ß-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, ß-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluaxapyroxad, Iprodione, Isopyrazam, Mepiquat-chloride, Metconazole, Metominostrobin, Paclobutrazole, Penthiopyrad., Picoxystrobin, Prochloraz, Prothioconazole, Pyraclostrobin, Tebuconazole, Thiophanate-methyl, Trifloxystrobin, Vinclozolin; Canola Insecticides: Carbofuran, Thiacloprid, Deltamethrin, Imidacloprid, Clothianidin, Thiamethoxam, Acetamiprid, Dinetofuran, ß-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

The following examples are offered by way of illustration and not by way of limitation.

EXPERIMENTAL EXAMPLES

Example 1. Discovery of Novel Pesticidal Genes from *Bacillus thuringiensis*

Novel pesticidal genes were identified from bacterial strains ATX47307 and ATX65002 using the following steps:

- Preparation of total DNA from the strain. Total DNA contains both genomic DNA and extrachromosomal DNA. Extrachromosomal DNA contains a mixture of some or all of the following: plasmids of various size; phage chromosomes; other uncharacterized extrachromosomal molecules.
- Sequencing of the DNA. Total DNA is sequenced via Next-Generation Sequencing methods.
- Identification of putative toxin genes via homology and/or other computational analyses.
- When required, sequence finishing of the gene of interest by one of several PCR or cloning strategies (e.g. TAIL-PCR).

TABLE 1

Novel gene identified from strain ATX47307

| Gene name | Molecular weight (kD) | Closest homolog | Nucleotide SEQ ID NO | Amino acid SEQ ID NO |
|---|---|---|---|---|
| Axmi477 | 132 | 75% Cry9Ba1 | 1 | 5 |
| Axmi477.2 | | | | 6 |
| Axmi477.3 | | | | 7 |
| Axmi477(trun) | | 60% Cry9Ba1(trun) | | 8 |
| Axmi477.2(trun) | | | | 9 |
| Axmi477.3(trun) | | | | 10 |

Axmi477.2 and Axmi477.3 represent proteins encoded from a downstream start site relative to Axmi477.

TABLE 2

Novel gene identified from strain ATX47307

| Gene name | Molecular weight (kD) | Closest homolog | Nucleotide SEQ ID NO | Amino acid SEQ ID NO |
|---|---|---|---|---|
| Axmi482 | 37 | 94% Axmi486; 51% | 2 | 11 |
| Axmi482.2 | Mtx3 | | | 12 |
| Axmi482.3 | | | | 13 |
| Axmi482.4 | | | | 14 |

Axmi482.2, Axmi482.3, and Axmi482.4 represent proteins encoded from a downstream start site relative to Axmi482.

TABLE 3

Novel gene identified from strain ATX65002

| Gene name | Molecular weight (kD) | Closest homolog | Nucleotide SEQ ID NO | Amino acid SEQ ID NO |
|---|---|---|---|---|
| Axmi486 | 38 | 94% Axmi482; | 3 | 15 |
| Axmi486.2 | | 49% Mtx3 | | 16 |
| Axmi486.3 | | | | 17 |
| Axmi486.4 | | | | 18 |
| Axmi486.5 | | | | 19 |

Axmi486.2, Axmi486.3, Axmi486.4, and Axmi486.5 represent proteins encoded from a downstream start site relative to Axmi486.

TABLE 4

Novel gene identified from strain ATX65002

| Gene name | Molecular weight (kD) | Closest homolog | Nucleotide SEQ ID NO | Amino acid SEQ ID NO |
|---|---|---|---|---|
| >Axmi525 | 38 | 97% Axmi486; | 4 | 20 |
| >Axmi525.2 | | 51% Mtx3 | | 21 |
| >Axmi525.3 | | | | 22 |
| >Axmi525.4 | | | | 23 |
| >Axmi525.5 | | | | 24 |
| >Axmi525.6 | | | | 25 |
| >Axmi525.7 | | | | 26 |

Axmi525.2, Axmi525.3, Axmi525.4, Axmi525.5, Axmi525.6, and Axmi525.7 represent proteins encoded from a downstream start site relative to Axmi525.

Example 2. Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, and then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests* and *Journal of Economic Entomology* or by discussion with members of the Entomological Society of America (ESA).

In some embodiments, the DNA regions encoding the toxin region of the pesticidal proteins disclosed herein are cloned into the *E. coli* expression vector pMAL-C4x behind the malE gene coding for Maltose binding protein (MBP). These in-frame fusions result in MBP-Axmi fusion proteins expression in *E. coli*.

For expression in *E. coli*, BL21*DE3 are transformed with individual plasmids. Single colonies are inoculated in LB supplemented with carbenicillin and glucose, and grown overnight at 37° C. The following day, fresh medium is inoculated with 1% of overnight culture and grown at 37° C. to logarithmic phase. Subsequently, cultures are induced with 0.3 mM IPTG overnight at 20° C. Each cell pellet is suspended in 20 mM Tris-Cl buffer, pH 7.4+200 mM NaCl+1 mM DTT+protease inhibitors and sonicated. Analysis by SDS-PAGE can be used to confirm expression of the fusion proteins.

Total cell free extracts are then run over amylose column attached to fast protein liquid chromatography (FPLC) for affinity purification of MBP-axmi fusion proteins. Bound fusion proteins are eluted from the resin with 10 mM maltose solution. Purified fusion proteins are then cleaved with either Factor Xa or trypsin to remove the amino terminal MBP tag from the Axmi protein. Cleavage and solubility of the proteins can be determined by SDS-PAGE Example 3. Expression and Purification Truncated variants of Axmi477 (which is set forth herein as SEQ ID NO:8), Axmi482 (which is set forth herein as SEQ ID NO:13), Axmi486 (which is set forth herein as SEQ ID NO:16), and Axmi525 (which is set forth herein as SEQ ID NO:26), were expressed and assayed for bioactivity. The genes were PCR amplified from their respective strains using HERCULASE® II Fusion DNA Polymerase with primers incorporating an AscI linker at the 3' end. Amplified PCR product was digested with AscI and ligated into the pMalC4X vector. The clones were confirmed by sequencing and transformed in Bl21 competent cells. A single colony of each was inoculated in LB media and grown at 37° C. until log phase, and induced with 0.5 mM IPTG at 20° C. for 18 hours. Purified protein was digested with Factor Xa at a 1:50 ratio at room temperature overnight. Purified protein was submitted to bioassay vs. selected insect pests according to standard protocol. The results are shown in Tables 5-8.

TABLE 5

Mortality and stunting scores for Axmi477

| Pest Group | Stunting Score | Mortality Percentage |
|---|---|---|
| Plutella xylostella (DBM) | 4 | 100 |
| Anticarsia gemmatalis (VBC) | 4 | 100 |
| Diatraea grandiosella (SWCB) | 3.5 | 25 |
| Diatraea saccharalis (SCB) | 3.5 | 0 |
| Heliothis virescens (Hv) | 4 | 75 |
| Heliocoverpa zea (Hz) | 2 | 25 |
| Ostrinia nublialis (ECB) | 3 | 25 |
| Spodoptera frugiperda (FAW) | 1 | 0 |
| Spodoptera exigua (BAW) | 3 | 0 |
| Agrotis ipsilon (BCW) | 4 | 0 |
| Pseudoplusia includens (SBL) | 4 | 100 |

TABLE 6

Mortality and stunting scores for Axmi482

| Pest Group | Stunting Score | Mortality Percentage |
|---|---|---|
| Plutella xylostella (DBM) | 4 | 100 |
| Anticarsia gemmatalis (VBC) | 4 | 75 |
| Diatraea grandiosella (SWCB) | 4 | 50 |
| Diatraea saccharalis (SCB) | 3 | 0 |
| Heliothis virescens (Hv) | 1 | 0 |
| Heliocoverpa zea (Hz) | 4 | 0 |
| Ostrinia nublialis (ECB) | 3 | 1 |
| Spodoptera frugiperda (FAW) | 3 | 0 |

TABLE 7

Mortality and stunting scores for Axmi486

| Pest Group | Stunting Score | Mortality Percentage |
|---|---|---|
| Plutella xylostella (DBM) | 4 | 100 |
| Anticarsia gemmatalis (VBC) | 4 | 37 |
| Diatraea grandiosella (SWCB) | 3.5 | 50 |
| Diatraea saccharalis (SCB) | 2.5 | 25 |
| Heliothis virescens (Hv) | 3.5 | 0 |
| Heliocoverpa zea (Hz) | 3 | 0 |
| Pseudoplusia includens (SBL) | 1 | 0 |

TABLE 8

Mortality and stunting scores for Axmi525

| Pest Group | Stunting Score | Mortality Percentage |
|---|---|---|
| Spodoptera frugiperda (FAW) | 1 | 0% |
| Heliothis virescens (Hv) | 1.5 | 0% |
| Helicoverpa zea (Hz) | 3 | 0% |
| Anticarsia gemmatalis (VBC) | 4 | 42% |
| Spodoptera eridania (SAW) | 3.2 | 70% |
| Plutella xylostella (DBM) | 4 | 100% |
| Diatraea grandiosella (SWCB) | 4 | 83% |
| Diatraea crambidoides (SCB) | 4 | 66% |

Stunting Score:
0—No activity
1—Non-uniform stunt
2—Slight uniform stunt
3—Strong uniform stunt
4—Severe uniform stunt Example 4. Vectoring of Genes for Plant Expression The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

In one aspect of the invention, synthetic DNA sequences are designed and generated. These synthetic sequences have altered nucleotide sequence relative to the parent sequence, but encode proteins that are essentially identical to the parent sequence.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:27) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL sequence (SEQ ID NO:27) at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 5. Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

DN62A5S Media

| Components | Per Liter | Source |
| --- | --- | --- |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 6. Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed.

The resulting mature somatic embryos are then placed under low light, and the process of regeneration is initiated as known in the art.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A construct comprising a heterologous promoter operably linked to a nucleotide sequence encoding an amino acid sequence having pesticidal activity against a lepidopteran pest, wherein said nucleotide sequence is selected from the group consisting of:
   a) the nucleotide sequence set forth in SEQ ID NO:1;
   b) a nucleotide sequence that encodes a polypeptide comprising the amino acid sequence of any one of SEQ ID NO:5-10;
   c) a nucleotide sequence that encodes a polypeptide comprising an amino acid sequence having at least 95% sequence identity to the amino acid sequence of any one of SEQ ID NO:5-10.

2. The construct of claim 1, wherein said nucleotide sequence is a synthetic sequence that has been designed for expression in a plant.

3. The construct of claim 1, wherein said promoter is capable of directing expression of said nucleotide sequence in a plant cell.

4. A vector comprising the construct of claim 1.

5. The vector of claim 4, further comprising a nucleic acid molecule encoding a heterologous polypeptide.

6. A host cell that contains the construct of claim 1.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the construct of claim 1.

12. A recombinant polypeptide with pesticidal activity against a lepidopteran pest, wherein said polypeptide comprises a heterologous leader or transit peptide and wherein said polypeptide is selected from the group consisting of:
   a) a polypeptide comprising the amino acid sequence of any one of SEQ ID NO:5-10; and
   b) a polypeptide comprising an amino acid sequence having at least 95% sequence identity to the amino acid sequence of any one of SEQ ID NO:5-10.

13. The polypeptide of claim 12 further comprising heterologous amino acid sequences.

14. A composition comprising the polypeptide of claim 12.

15. The composition of claim 14, wherein said composition is selected from the group consisting of a powder, dust, pellet, granule, spray, emulsion, colloid, and solution.

16. The composition of claim 14, wherein said composition is prepared by desiccation, lyophilization, homogenization, extraction, filtration, centrifugation, sedimentation, or concentration of a culture of bacterial cells.

17. The composition of claim 14, comprising from about 1% to about 99% by weight of said polypeptide.

18. A method for controlling a lepidopteran pest population comprising contacting said population with a pesticidally-effective amount of the polypeptide of claim 12.

19. A method for killing a lepidopteran pest, comprising contacting said pest with, or feeding to said pest, a pesticidally-effective amount of the polypeptide of claim 12.

20. A method for producing a polypeptide with pesticidal activity against a lepidopteran pest, comprising culturing the host cell of claim 6 under conditions in which the nucleic acid molecule encoding the polypeptide is expressed.

21. A plant or plant cell having stably incorporated into its genome a DNA construct comprising a nucleotide sequence that encodes a protein having pesticidal activity against a lepidopteran pest, wherein said nucleotide sequence is selected from the group consisting of:
   a) the nucleotide sequence set forth in SEQ ID NO:1;
   b) a nucleotide sequence that encodes a polypeptide comprising the amino acid sequence of any one of SEQ ID NO:5-10; and
   c) a nucleotide sequence that encodes a polypeptide comprising an amino acid sequence having at least 95% sequence identity to the amino acid sequence of any one of SEQ ID NO:5-10.

22. A method for protecting a plant from a lepidopteran pest, comprising expressing in a plant or cell thereof a nucleotide sequence that encodes a pesticidal polypeptide, wherein said nucleotide sequence is selected from the group consisting of:
   a) the nucleotide sequence set forth in SEQ ID NO:1;
   b) a nucleotide sequence that encodes a polypeptide comprising the amino acid sequence of any one of SEQ ID NO:5-10; and
   c) a nucleotide sequence that encodes a polypeptide comprising an amino acid sequence having at least 95% sequence identity to the amino acid sequence of any one of SEQ ID NO:5-10.

23. The method of claim 22, wherein said plant produces a pesticidal polypeptide having pesticidal activity against a lepidopteran pest.

24. A method for increasing yield in a plant comprising growing in a field a plant or a seed thereof having stably incorporated into its genome a DNA construct comprising a nucleotide sequence that encodes a protein having pesticidal activity against a lepidopteran pest, wherein said nucleotide sequence is selected from the group consisting of:
   a) the nucleotide sequence set forth in SEQ ID NO:1;
   b) a nucleotide sequence that encodes a polypeptide comprising the amino acid sequence of any one of SEQ ID NO:5-10; and
   c) a nucleotide sequence that encodes a polypeptide comprising an amino acid sequence having at least 95% sequence identity to the amino acid sequence of any one of SEQ ID NO:5-10;
wherein said field is infested with a lepidopteran pest against which said polypeptide has pesticidal activity and wherein said yield is increased relative to the yield of a plant that does not express a nucleotide sequence encoding any one of SEQ ID NO:5-10.

* * * * *

SEQUENCE LISTING

```
<160> NUMBER OF SEQ ID NOS: 27

<210> SEQ ID NO 1
<211> LENGTH: 3695
<212> TYPE: DNA
<213> ORGANISM: Bacillus thuringiensis

<400> SEQUENCE: 1
atgaatcgaa ataatcaagg tgaatatgaa attattgacg cttccacttg tggttgttcg      60
tcagatgatg ttgttcaata tcctttggca agagatccga atgctgcatt ccaaaatatg     120
aattataaag attatttgaa aatgtctgac ggagactacg tcgattctta tataaaccca     180
ggcttatcta ttggtcgtag agatgtgacc ctaactggag ttggtattgt tgcgctaata     240
gtagggactt taggtggtcc agttgggggt atagtaactg gcttgatttc ctctctttta     300
ggattattgt ggccaagtaa tgataatgat gtatgggaag cttttatggc acaaatagaa     360
gagctaattg aacaaaggat agcagatcaa gtagtaagga atgcactcga taacttaact     420
ggattgcgcg attattataa tcaataccta ttagcattgg aggagtggca ggaaaggccg     480
aacgctgtaa gatctacctt agtttttaat agatttgaaa ccctgcattc tcactttgta     540
actagtatgc caagctttgg tagtggccct ggaagtgaaa ggtatgcggt acaattgctg     600
acagtttatg cacaagcggc aaatctgcat ttgttattat taagagatgc tgacatttat     660
ggggcaaggt ggggacttcg tgaatctcag attgatttat attttaatga gctacaaaat     720
cgtactcgag attataccaa tcattgtgta actgcgtaca ataatgggtt agaggagata     780
cgaggaacaa gccctgcaag ttggttgagg taccatcaat tccgtagaga gacaacacta     840
atagcattgg atttagtggc gatattccca tattacaacg tacgagaata tccaattggg     900
gtaaatcctc agcttacacg tgatgtatat acagatccaa taggggttac tttcagaaga     960
gaagattggg aaacaggagt agaatgcaga ccatgggtaa atactcctta catgagcttt    1020
tcggatcttg aaaatgcaat aattcgtcca ccacatctat ttgaaacatt acgtaattta    1080
acaattcata caggtcgata taacctagta ggaggggcga gatttattga aggatgggtc    1140
ggacattctg taacaaatac tcgcttgggt aattcaacag tatttacaag taattatggt    1200
tctttgccac ctcgttttca agtttttaat tttactaatt ttgatgttta ccaaattaat    1260
acgagagcag attctacagg tacctttaga atccctggat ttgcagttac aagggcccaa    1320
ttcattccgg gtgggactta ttcagtagct caccgagatc caggggcatg tcaacaagat    1380
tatgattcaa ttgaagagtt accaagtcta gacccggatg aacctattaa tagaagttat    1440
agtcatagat tatcgcatgt taccctttat aaatatactc tctcagatac agattatgga    1500
gttatcaatt atacagatta tggaagtatg cctgcatatg tctggacaca tcgcgatgtg    1560
gaccttacta acacgattac tgcagataga attacacaac tcccattagt aaaggcatct    1620
acactacctg cgggtactac tgtggtaaaa ggcccaggat ttacaggagg agatatactc    1680
cgaagaacaa ctaatggaac atttgggaca ttacatgtaa gggttaattc accattaaca    1740
```

```
caacaatatc gcctaagagt tcgttttgcc tcaacaggaa atttcagtat aagggtactc    1800
cgtggaggga cttctatcgg tgatgctaga tttgggagca caatgaacag aggacaggaa    1860
ctaacttacg aatcctttgt cacaagagag tttactacta ctggtccgtt caatccgcct    1920
tttacattta cacaaactca agaaattcta acagtgaatg cagaaggtgt tagcaccggt    1980
ggtgaatatt atatagatag tattgagatt gttcctgtaa atccgacgcg agaggcggaa    2040
gaggatctag aagcagcgaa gaaagcggtg gcgagcttgt ttacacgtac aagggacgga    2100
ttacaagtaa atgtgacaga ttatcaagtc gatcaagcgg caaatttagt gtcatgctta    2160
tcagatgaac aatatgggca tgacaaaaag atgttattgg aagcggtaag agcggcaaaa    2220
cgcctcagcc gagaacgcaa cttacttcag gatccagatt ttaatacaat caatagtaca    2280
gaagaaaatg gatggaaagc aagtaacggc gttactatta gcgagggcgg tccattctat    2340
aaaggccgtg cgcttcagct agcaagcgca agagaaaatt acccaacata catttatcaa    2400
aaagtaaatg catcagagtt aaagccgtat acacgttata gactggatgg gttcgtgaag    2460
agtagtcaag atttagaaat tgatctcatt caccatcata agtccatctc gtgaaaaat    2520 gtaccagata atttagtatc cgatacttac tcggatggtt cttgcagtgg aatgaatcga    2580
tgtgaggaac aacagatggt aaatgcgcaa ctggaaacag aacatcatca tccgatggat    2640
tgctgtgaag cggctcaaac acatgagttt tcttcctata ttaatacagg cgatctaaat    2700
tcaagtgtag atcaaggcat ttgggttgta ttgaaagttc gaacaaccga tggttatgcg    2760
acgctaggaa tcttgaatt ggtagaggtc ggaccgttat cgggtgaatc tctagaacgt    2820
gaacaaaggg ataatgcgaa atggagtgca gagctaggaa gaaagcgtgc agaaacagat    2880
cgcgtgtatc aagatgccaa acaatccatc aatcatttat ttgtggatta tcaagatcaa    2940
caattaaatc cagaaatagg gatggcagat attattgacg ctcaaaatct tgtcgcatca    3000
atttcagatg tgtatagcga tgcagtactg caaatccctg gaattaacta tgagatttac    3060
acagagctat ccaatcgctt acaacaagca tcgtatctgt atacgtctcg aaatgcggtg    3120
caaaatgggg actttaacag cggtctagat agttggaatg caacaggggg ggctacggta    3180
caacaggatg gcaatacgca tttcttagtt cttttctcatt gggatgcaca agtttctcaa    3240
caatttagag tgcagccgaa ttgtaaatat gtattacgtg taacagcaga gaaagtaggc    3300
ggcggagacg gatacgtgac aatccgggat ggtgctcatc atacagaaaa gcttacattt    3360
aatgcatgtg attatgatat aaatggcacg tacgtgactg ataatacgta tctaacaaaa    3420
gaagtggtat tctattcaca tacagaacac atgtgggtag aggtaagtga aacagaaggt    3480
gcatttcata tagatagtat tgaattcgtt gaaacagaaa agtaacggga tgatgttccg    3540
aacatataag gtataaggaa cgatacgccg tataaaagat tctcaaacag aatgtgaaat    3600
aaatgaggac ccctccgggt agtcgtacat ggaaagtaca cgactacccg gagggtattt    3660
tttatataaa aaatgtggtt tttcactacg gtcta                              3695

<210> SEQ ID NO 2
<211> LENGTH: 1008
<212> TYPE: DNA
<213> ORGANISM: Bacillus thuringiensis

<400> SEQUENCE: 2
atgaataaaa aagtaacaaa aacagtatta agcgtggtaa tgggtataag tgttttagca      60
tctcctttag ctgtagccgc aaaaacagag aataataaag aacaacaagt aattacacag     120
tttaatcaga gagaaaataa gttccctgat gtaggacagg ggattcaatg gttatctcaa     180
```

```
ttttatggaa aatctttaaa gaataatggt gaaggatact ccttaggtaa tgatgtaatg      240
agctattttt tagaagtaaa gaattcttat ggtcaattgg caatagaacc tcaagtaata      300
agcactacac ctctttgggc tggccaaagc gacttggaaa atgcaactga tcatgaacaa      360
actttaaatt ccacagaatt taaaaaaacg tattctaaca caaccaccac ctctacagaa      420
aatggattta tgataggtca ggaaaccgaa gggaaagttg gtatacccct tgtcgcagaa      480
ggaaaagtca ccataaaaac tgaatataac tttaatcata ctaatgggta tgaaacatct      540
gaaagtgtag agtatattgc tccttctcaa tctattaagg taccaccgca tactattgcc      600
cgagtgacag cattattaga tgtgaaaaaa attaaaggaa agatgcatct atattcagaa      660
attgggctta ataagagatta tggttacgat atggtgccac ttgttttataa atatggagga      720 ccatttaagt atgtaacctt aggcacatta tatgacgagg gctataagca ggcacaatta      780
gattattcca atatgggaaa tgttataccg aagaaattg agactgtttc gaaaagtaac      840
aatcccaacc atttattagc aagtggatta ggaatctttg aatcagaata cggaagtgta      900
tttaatgtta agttgaata cattaatatt aaaactaaaa agattgaaaa aacagagaat      960
cttactattg aacctacaat agtccctgtt gaaaagacga atacaaaa                  1008

<210> SEQ ID NO 3
<211> LENGTH: 1023
<212> TYPE: DNA
<213> ORGANISM: Bacillus thuringiensis

<400> SEQUENCE: 3
gtgagggaga aggatttgaa taaaaaagta acaaaggcag tattaagcat gatagtgggt       60
ataagtgttt tagcatctcc tttagctgta gccgcaaaaa cagagaataa taagaacaa      120 caagtaatta cacattttaa tcagagagaa ataagttcc ctgatgtagg acaggggatt      180
caatggttat ctcaatttta tggaaagtct ttaagaata atggtgaagg atactccctta    240 ggtcaggatg taatgagata ttttttagaa gtaagaatt cttacggtca attggcaatg      300
gaacctcaag taataagcac tacacctctt tgggccggcc aaagtgactt ggaaaatgca      360
actgatcatg aacaaacttt aaattccaca gaatttaaaa aaacgtattc taacacaaca      420
accacctcta cagaaaatgg atttatgata ggtcaagaga ctgaagggaa agttggtatt      480 cccttttgtcg cagaaggaaa agtcaccata aaaactgaat ataactttaa tcatactaat      540
gggtatgaaa catctgaaag tgtagagtat attgctcctt ctcaatctat taaggtacca      600
ccgcatacta ttgcccgagt gacagcatta ttagatgtga aaaaatcaa agggaaaatg      660 catctatatt cagaaattgg gcttaataaa gattatggtt acgatatggt gccacttgtt      720
tataaatatg gaggtccatt taagtatgta accttaggca cattatatga cgagggctat      780
aagcaggcac aattagatta tttcaatatg ggaaatgtta taccggaaga aattgagact      840
gtttcaaaaa gtaacaatcc caaccattta ttagcaagtg gagtaggaat ctttgaatca      900
gaatacggaa gtgtatttaa tgttaaagtt gaatacatta atattaatac gaaaaagatt      960
gaaaaaacag agaatcttac tattgaacct acaatagtcc ctgttaaaca gacgaataca     1020
aaa                                                                  1023

<210> SEQ ID NO 4
<211> LENGTH: 1029
<212> TYPE: DNA
<213> ORGANISM: Bacillus thuringiensis
```

-continued

<400> SEQUENCE: 4

```
gtgagggaga aagatatgga taaaaaaata acaaaagcag cgttaagcat gataatgggt      60
ataagtgttt tatcatctcc tttagctgta gccgcaaaaa cagagaataa taaagaacaa     120
cacgtaatta cacagtttaa tcagagagaa aataagttcc ctgatgtagg acaggggatt     180
caatggttat ctcaatttta tggaaaatct ttaaagaata atggggaagg atactcctta     240
ggtcaggatg taatgagcta ttttctagaa gtaaaaaatt cttatggtca attggcaatg     300
gaacctcaag taataagcac tacacctctt tgggctggcc aaagtgactt ggaaaatgca     360
actgatcatg aacaaacttt aaattccaca gaatttaaaa aaacgtattc taacacaaca     420
accacctcta cagaaaatgg atttatgata ggtcaagaga ctgaagggaa agttggtatt     480
ccctttgtcg cagaaggaaa agtcaccata aaaactgaat ataactttaa tcatactaat     540
gggtatgaaa catctgaaag tgtagagtat attgctcctt ctcaatctat taaggtacca     600
ccgcatacta ttgcccgagt gacagcatta ttagatgtga aaaaaatcaa agggaaaatg     660
catctatatt cagaaattgg gcttaataaa gattatggtt acgatatggt gccacttgtt     720
tataaatatg gaggtccatt taagtatgta accttaggca cattatatga cgagggctat     780
aagcaggcac aattagatta tttcaatatg ggaaatgtta taccggaaga aattgagact     840
gtttcaaaaa gtaacaatcc caaccattta ttagcaagtg gagtaggaat ctttgaatca     900
gaatacggaa gtgtatttaa tgttaaagtt gaatacatta atattaatac gaaaaagatt     960
gaaaaaacag agaatcttac tattgaacct acaatagtcc ctgttaaaca gacgaatacg    1020
aatacaaaa                                                            1029
```

<210> SEQ ID NO 5
<211> LENGTH: 1174
<212> TYPE: PRT
<213> ORGANISM: Bacillus thuringiensis

<400> SEQUENCE: 5

```
Met Asn Arg Asn Asn Gln Gly Glu Tyr Glu Ile Ile Asp Ala Ser Thr
1               5                   10                  15

Cys Gly Cys Ser Ser Asp Asp Val Val Gln Tyr Pro Leu Ala Arg Asp
            20                  25                  30

Pro Asn Ala Ala Phe Gln Asn Met Asn Tyr Lys Asp Tyr Leu Lys Met
        35                  40                  45

Ser Asp Gly Asp Tyr Val Asp Ser Tyr Ile Asn Pro Gly Leu Ser Ile
    50                  55                  60

Gly Arg Arg Asp Val Thr Leu Thr Gly Val Gly Ile Val Ala Leu Ile
65                  70                  75                  80

Val Gly Thr Leu Gly Gly Pro Val Gly Gly Ile Val Thr Gly Leu Ile
                85                  90                  95

Ser Ser Leu Leu Gly Leu Leu Trp Pro Ser Asn Asp Asn Asp Val Trp
            100                 105                 110

Glu Ala Phe Met Ala Gln Ile Glu Glu Leu Ile Glu Gln Arg Ile Ala
        115                 120                 125

Asp Gln Val Val Arg Asn Ala Leu Asp Asn Leu Thr Gly Leu Arg Asp
    130                 135                 140

Tyr Tyr Asn Gln Tyr Leu Leu Ala Leu Glu Glu Trp Gln Glu Arg Pro
145                 150                 155                 160

Asn Ala Val Arg Ser Thr Leu Val Phe Asn Arg Phe Glu Thr Leu His
                165                 170                 175
```

-continued

```
Ser His Phe Val Thr Ser Met Pro Ser Phe Gly Ser Gly Pro Gly Ser
            180                 185                 190

Glu Arg Tyr Ala Val Gln Leu Leu Thr Val Tyr Ala Gln Ala Ala Asn
            195                 200                 205

Leu His Leu Leu Leu Leu Arg Asp Ala Asp Ile Tyr Gly Ala Arg Trp
            210                 215                 220

Gly Leu Arg Glu Ser Gln Ile Asp Leu Tyr Phe Asn Glu Leu Gln Asn
225                 230                 235                 240

Arg Thr Arg Asp Tyr Thr Asn His Cys Val Thr Ala Tyr Asn Asn Gly
            245                 250                 255

Leu Glu Glu Ile Arg Gly Thr Ser Pro Ala Ser Trp Leu Arg Tyr His
            260                 265                 270

Gln Phe Arg Arg Glu Thr Thr Leu Ile Ala Leu Asp Leu Val Ala Ile
            275                 280                 285

Phe Pro Tyr Tyr Asn Val Arg Glu Tyr Pro Ile Gly Val Asn Pro Gln
            290                 295                 300

Leu Thr Arg Asp Val Tyr Thr Asp Pro Ile Gly Val Thr Phe Arg Arg
305                 310                 315                 320

Glu Asp Trp Glu Thr Gly Val Glu Cys Arg Pro Trp Val Asn Thr Pro
            325                 330                 335

Tyr Met Ser Phe Ser Asp Leu Glu Asn Ala Ile Ile Arg Pro Pro His
            340                 345                 350

Leu Phe Glu Thr Leu Arg Asn Leu Thr Ile His Thr Gly Arg Tyr Asn
            355                 360                 365

Leu Val Gly Gly Ala Arg Phe Ile Glu Gly Trp Val Gly His Ser Val
            370                 375                 380

Thr Asn Thr Arg Leu Gly Asn Ser Thr Val Phe Thr Ser Asn Tyr Gly
385                 390                 395                 400

Ser Leu Pro Pro Arg Phe Gln Val Phe Asn Phe Thr Asn Phe Asp Val
            405                 410                 415

Tyr Gln Ile Asn Thr Arg Ala Asp Ser Thr Gly Thr Phe Arg Ile Pro
            420                 425                 430

Gly Phe Ala Val Thr Arg Ala Gln Phe Ile Pro Gly Gly Thr Tyr Ser
            435                 440                 445

Val Ala His Arg Asp Pro Gly Ala Cys Gln Gln Asp Tyr Asp Ser Ile
450                 455                 460

Glu Glu Leu Pro Ser Leu Asp Pro Asp Glu Pro Ile Asn Arg Ser Tyr
465                 470                 475                 480

Ser His Arg Leu Ser His Val Thr Leu Tyr Lys Tyr Thr Leu Ser Asp
            485                 490                 495

Thr Asp Tyr Gly Val Ile Asn Tyr Thr Asp Tyr Gly Ser Met Pro Ala
            500                 505                 510

Tyr Val Trp Thr His Arg Asp Val Asp Leu Thr Asn Thr Ile Thr Ala
            515                 520                 525

Asp Arg Ile Thr Gln Leu Pro Leu Val Lys Ala Ser Thr Leu Pro Ala
            530                 535                 540

Gly Thr Thr Val Val Lys Gly Pro Gly Phe Thr Gly Gly Asp Ile Leu
545                 550                 555                 560

Arg Arg Thr Thr Asn Gly Thr Phe Gly Thr Leu His Val Arg Val Asn
            565                 570                 575

Ser Pro Leu Thr Gln Gln Tyr Arg Leu Arg Val Arg Phe Ala Ser Thr
            580                 585                 590

Gly Asn Phe Ser Ile Arg Val Leu Arg Gly Gly Thr Ser Ile Gly Asp
```

-continued

```
            595                 600                 605
Ala Arg Phe Gly Ser Thr Met Asn Arg Gly Gln Glu Leu Thr Tyr Glu
    610                 615                 620
Ser Phe Val Thr Arg Glu Phe Thr Thr Thr Gly Pro Phe Asn Pro Pro
625                 630                 635                 640
Phe Thr Phe Thr Gln Thr Gln Glu Ile Leu Thr Val Asn Ala Glu Gly
                    645                 650                 655
Val Ser Thr Gly Gly Glu Tyr Tyr Ile Asp Ser Ile Glu Ile Val Pro
                660                 665                 670
Val Asn Pro Thr Arg Glu Ala Glu Asp Leu Glu Ala Ala Lys Lys
            675                 680                 685
Ala Val Ala Ser Leu Phe Thr Arg Thr Arg Asp Gly Leu Gln Val Asn
    690                 695                 700
Val Thr Asp Tyr Gln Val Asp Gln Ala Ala Asn Leu Val Ser Cys Leu
705                 710                 715                 720
Ser Asp Glu Gln Tyr Gly His Asp Lys Lys Met Leu Leu Glu Ala Val
                    725                 730                 735
Arg Ala Ala Lys Arg Leu Ser Arg Glu Arg Asn Leu Leu Gln Asp Pro
                740                 745                 750
Asp Phe Asn Thr Ile Asn Ser Thr Glu Glu Asn Gly Trp Lys Ala Ser
            755                 760                 765
Asn Gly Val Thr Ile Ser Glu Gly Gly Pro Phe Tyr Lys Gly Arg Ala
    770                 775                 780
Leu Gln Leu Ala Ser Ala Arg Glu Asn Tyr Pro Thr Tyr Ile Tyr Gln
785                 790                 795                 800
Lys Val Asn Ala Ser Glu Leu Lys Pro Tyr Thr Arg Tyr Arg Leu Asp
                    805                 810                 815
Gly Phe Val Lys Ser Ser Gln Asp Leu Glu Ile Asp Leu Ile His His
                820                 825                 830
His Lys Val His Leu Val Lys Asn Val Pro Asp Asn Leu Val Ser Asp
            835                 840                 845
Thr Tyr Ser Asp Gly Ser Cys Ser Gly Met Asn Arg Cys Glu Glu Gln
    850                 855                 860
Gln Met Val Asn Ala Gln Leu Glu Thr Glu His His His Pro Met Asp
865                 870                 875                 880
Cys Cys Glu Ala Ala Gln Thr His Glu Phe Ser Ser Tyr Ile Asn Thr
                    885                 890                 895
Gly Asp Leu Asn Ser Ser Val Asp Gln Gly Ile Trp Val Val Leu Lys
                900                 905                 910
Val Arg Thr Thr Asp Gly Tyr Ala Thr Leu Gly Asn Leu Glu Leu Val
            915                 920                 925
Glu Val Gly Pro Leu Ser Gly Glu Ser Leu Glu Arg Glu Gln Arg Asp
    930                 935                 940
Asn Ala Lys Trp Ser Ala Glu Leu Gly Arg Lys Arg Ala Glu Thr Asp
945                 950                 955                 960
Arg Val Tyr Gln Asp Ala Lys Gln Ser Ile Asn His Leu Phe Val Asp
                    965                 970                 975
Tyr Gln Asp Gln Gln Leu Asn Pro Glu Ile Gly Met Ala Asp Ile Ile
                980                 985                 990
Asp Ala Gln Asn Leu Val Ala Ser Ile Ser Asp Val Tyr Ser Asp Ala
            995                 1000                1005
Val Leu Gln Ile Pro Gly Ile Asn Tyr Glu Ile Tyr Thr Glu Leu
    1010                1015                1020
```

Ser Asn Arg Leu Gln Gln Ala Ser Tyr Leu Tyr Thr Ser Arg Asn
1025                1030                1035

Ala Val Gln Asn Gly Asp Phe Asn Ser Gly Leu Asp Ser Trp Asn
1040                1045                1050

Ala Thr Gly Gly Ala Thr Val Gln Gln Asp Gly Asn Thr His Phe
1055                1060                1065

Leu Val Leu Ser His Trp Asp Ala Gln Val Ser Gln Gln Phe Arg
1070                1075                1080

Val Gln Pro Asn Cys Lys Tyr Val Leu Arg Val Thr Ala Glu Lys
1085                1090                1095

Val Gly Gly Gly Asp Gly Tyr Val Thr Ile Arg Asp Gly Ala His
1100                1105                1110

His Thr Glu Lys Leu Thr Phe Asn Ala Cys Asp Tyr Asp Ile Asn
1115                1120                1125

Gly Thr Tyr Val Thr Asp Asn Thr Tyr Leu Thr Lys Glu Val Val
1130                1135                1140

Phe Tyr Ser His Thr Glu His Met Trp Val Glu Val Ser Glu Thr
1145                1150                1155

Glu Gly Ala Phe His Ile Asp Ser Ile Glu Phe Val Glu Thr Glu
1160                1165                1170

Lys

<210> SEQ ID NO 6
<211> LENGTH: 1135
<212> TYPE: PRT
<213> ORGANISM: Bacillus thuringiensis

<400> SEQUENCE: 6

Met Asn Tyr Lys Asp Tyr Leu Lys Met Ser Asp Gly Asp Tyr Val Asp
1               5                   10                  15

Ser Tyr Ile Asn Pro Gly Leu Ser Ile Gly Arg Arg Asp Val Thr Leu
                20                  25                  30

Thr Gly Val Gly Ile Val Ala Leu Ile Val Gly Thr Leu Gly Gly Pro
            35                  40                  45

Val Gly Gly Ile Val Thr Gly Leu Ile Ser Ser Leu Leu Gly Leu Leu
        50                  55                  60

Trp Pro Ser Asn Asp Asn Asp Val Trp Glu Ala Phe Met Ala Gln Ile
65                  70                  75                  80

Glu Glu Leu Ile Glu Gln Arg Ile Ala Asp Gln Val Val Arg Asn Ala
                85                  90                  95

Leu Asp Asn Leu Thr Gly Leu Arg Asp Tyr Tyr Asn Gln Tyr Leu Leu
            100                 105                 110

Ala Leu Glu Glu Trp Gln Glu Arg Pro Asn Ala Val Arg Ser Thr Leu
        115                 120                 125

Val Phe Asn Arg Phe Glu Thr Leu His Ser His Phe Val Thr Ser Met
    130                 135                 140

Pro Ser Phe Gly Ser Gly Pro Gly Ser Glu Arg Tyr Ala Val Gln Leu
145                 150                 155                 160

Leu Thr Val Tyr Ala Gln Ala Ala Asn Leu His Leu Leu Leu Leu Arg
                165                 170                 175

Asp Ala Asp Ile Tyr Gly Ala Arg Trp Gly Leu Arg Glu Ser Gln Ile
            180                 185                 190

Asp Leu Tyr Phe Asn Glu Leu Gln Asn Arg Thr Arg Asp Tyr Thr Asn
        195                 200                 205

-continued

His Cys Val Thr Ala Tyr Asn Asn Gly Leu Glu Glu Ile Arg Gly Thr
    210                 215                 220

Ser Pro Ala Ser Trp Leu Arg Tyr His Gln Phe Arg Arg Glu Thr Thr
225                 230                 235                 240

Leu Ile Ala Leu Asp Leu Val Ala Ile Phe Pro Tyr Tyr Asn Val Arg
                245                 250                 255

Glu Tyr Pro Ile Gly Val Asn Pro Gln Leu Thr Arg Asp Val Tyr Thr
            260                 265                 270

Asp Pro Ile Gly Val Thr Phe Arg Arg Glu Asp Trp Glu Thr Gly Val
        275                 280                 285

Glu Cys Arg Pro Trp Val Asn Thr Pro Tyr Met Ser Phe Ser Asp Leu
    290                 295                 300

Glu Asn Ala Ile Ile Arg Pro Pro His Leu Phe Glu Thr Leu Arg Asn
305                 310                 315                 320

Leu Thr Ile His Thr Gly Arg Tyr Asn Leu Val Gly Gly Ala Arg Phe
                325                 330                 335

Ile Glu Gly Trp Val Gly His Ser Val Thr Asn Thr Arg Leu Gly Asn
            340                 345                 350

Ser Thr Val Phe Thr Ser Asn Tyr Gly Ser Leu Pro Pro Arg Phe Gln
        355                 360                 365

Val Phe Asn Phe Thr Asn Phe Asp Val Tyr Gln Ile Asn Thr Arg Ala
    370                 375                 380

Asp Ser Thr Gly Thr Phe Arg Ile Pro Gly Phe Ala Val Thr Arg Ala
385                 390                 395                 400

Gln Phe Ile Pro Gly Gly Thr Tyr Ser Val Ala His Arg Asp Pro Gly
                405                 410                 415

Ala Cys Gln Gln Asp Tyr Asp Ser Ile Glu Glu Leu Pro Ser Leu Asp
            420                 425                 430

Pro Asp Glu Pro Ile Asn Arg Ser Tyr Ser His Arg Leu Ser His Val
        435                 440                 445

Thr Leu Tyr Lys Tyr Thr Leu Ser Asp Thr Asp Tyr Gly Val Ile Asn
    450                 455                 460

Tyr Thr Asp Tyr Gly Ser Met Pro Ala Tyr Val Trp Thr His Arg Asp
465                 470                 475                 480

Val Asp Leu Thr Asn Thr Ile Thr Ala Asp Arg Ile Thr Gln Leu Pro
                485                 490                 495

Leu Val Lys Ala Ser Thr Leu Pro Ala Gly Thr Thr Val Val Lys Gly
            500                 505                 510

Pro Gly Phe Thr Gly Gly Asp Ile Leu Arg Arg Thr Thr Asn Gly Thr
        515                 520                 525

Phe Gly Thr Leu His Val Arg Val Asn Ser Pro Leu Thr Gln Gln Tyr
    530                 535                 540

Arg Leu Arg Val Arg Phe Ala Ser Thr Gly Asn Phe Ser Ile Arg Val
545                 550                 555                 560

Leu Arg Gly Gly Thr Ser Ile Gly Asp Ala Arg Phe Gly Ser Thr Met
                565                 570                 575

Asn Arg Gly Gln Glu Leu Thr Tyr Glu Ser Phe Val Thr Arg Glu Phe
            580                 585                 590

Thr Thr Thr Gly Pro Phe Asn Pro Pro Phe Thr Phe Thr Gln Thr Gln
        595                 600                 605

Glu Ile Leu Thr Val Asn Ala Glu Gly Val Ser Thr Gly Gly Glu Tyr
    610                 615                 620

-continued

Tyr Ile Asp Ser Ile Glu Ile Val Pro Val Asn Pro Thr Arg Glu Ala
625                 630                 635                 640

Glu Glu Asp Leu Glu Ala Ala Lys Lys Ala Val Ala Ser Leu Phe Thr
            645                 650                 655

Arg Thr Arg Asp Gly Leu Gln Val Asn Val Thr Asp Tyr Gln Val Asp
        660                 665                 670

Gln Ala Ala Asn Leu Val Ser Cys Leu Ser Asp Glu Gln Tyr Gly His
    675                 680                 685

Asp Lys Lys Met Leu Leu Glu Ala Val Arg Ala Ala Lys Arg Leu Ser
690                 695                 700

Arg Glu Arg Asn Leu Leu Gln Asp Pro Asp Phe Asn Thr Ile Asn Ser
705                 710                 715                 720

Thr Glu Glu Asn Gly Trp Lys Ala Ser Asn Gly Val Thr Ile Ser Glu
                725                 730                 735

Gly Gly Pro Phe Tyr Lys Gly Arg Ala Leu Gln Leu Ala Ser Ala Arg
            740                 745                 750

Glu Asn Tyr Pro Thr Tyr Ile Tyr Gln Lys Val Asn Ala Ser Glu Leu
        755                 760                 765

Lys Pro Tyr Thr Arg Tyr Arg Leu Asp Gly Phe Val Lys Ser Ser Gln
    770                 775                 780

Asp Leu Glu Ile Asp Leu Ile His His His Lys Val His Leu Val Lys
785                 790                 795                 800

Asn Val Pro Asp Asn Leu Val Ser Asp Thr Tyr Ser Asp Gly Ser Cys
                805                 810                 815

Ser Gly Met Asn Arg Cys Glu Glu Gln Gln Met Val Asn Ala Gln Leu
            820                 825                 830

Glu Thr Glu His His His Pro Met Asp Cys Cys Glu Ala Ala Gln Thr
        835                 840                 845

His Glu Phe Ser Ser Tyr Ile Asn Thr Gly Asp Leu Asn Ser Ser Val
    850                 855                 860

Asp Gln Gly Ile Trp Val Val Leu Lys Val Arg Thr Thr Asp Gly Tyr
865                 870                 875                 880

Ala Thr Leu Gly Asn Leu Glu Leu Val Glu Val Gly Pro Leu Ser Gly
                885                 890                 895

Glu Ser Leu Glu Arg Glu Gln Arg Asp Asn Ala Lys Trp Ser Ala Glu
            900                 905                 910

Leu Gly Arg Lys Arg Ala Glu Thr Asp Arg Val Tyr Gln Asp Ala Lys
        915                 920                 925

Gln Ser Ile Asn His Leu Phe Val Asp Tyr Gln Asp Gln Gln Leu Asn
    930                 935                 940

Pro Glu Ile Gly Met Ala Asp Ile Ile Asp Ala Gln Asn Leu Val Ala
945                 950                 955                 960

Ser Ile Ser Asp Val Tyr Ser Asp Ala Val Leu Gln Ile Pro Gly Ile
                965                 970                 975

Asn Tyr Glu Ile Tyr Thr Glu Leu Ser Asn Arg Leu Gln Gln Ala Ser
            980                 985                 990

Tyr Leu Tyr Thr Ser Arg Asn Ala Val Gln Asn Gly Asp Phe Asn Ser
        995                 1000                1005

Gly Leu Asp Ser Trp Asn Ala Thr Gly Gly Ala Thr Val Gln Gln
        1010                1015                1020

Asp Gly Asn Thr His Phe Leu Val Leu Ser His Trp Asp Ala Gln
        1025                1030                1035

Val Ser Gln Gln Phe Arg Val Gln Pro Asn Cys Lys Tyr Val Leu

-continued 1040                1045                1050

Arg Val  Thr Ala Glu Lys Val  Gly Gly Gly Asp Gly  Tyr Val Thr
    1055                1060                1065

Ile Arg  Asp Gly Ala His His  Thr Glu Lys Leu Thr  Phe Asn Ala
    1070                1075                1080

Cys Asp  Tyr Asp Ile Asn Gly  Thr Tyr Val Thr Asp  Asn Thr Tyr
    1085                1090                1095

Leu Thr  Lys Glu Val Val Phe  Tyr Ser His Thr Glu  His Met Trp
    1100                1105                1110

Val Glu  Val Ser Glu Thr Glu  Gly Ala Phe His Ile  Asp Ser Ile
    1115                1120                1125

Glu Phe  Val Glu Thr Glu Lys
    1130                1135

<210> SEQ ID NO 7
<211> LENGTH: 1127
<212> TYPE: PRT
<213> ORGANISM: Bacillus thuringiensis

<400> SEQUENCE: 7

Met Ser Asp Gly Asp Tyr Val Asp Ser Tyr Ile Asn Pro Gly Leu Ser
1               5                   10                  15

Ile Gly Arg Arg Asp Val Thr Leu Thr Gly Val Gly Ile Val Ala Leu
            20                  25                  30

Ile Val Gly Thr Leu Gly Gly Pro Val Gly Gly Ile Val Thr Gly Leu
        35                  40                  45

Ile Ser Ser Leu Leu Gly Leu Leu Trp Pro Ser Asn Asp Asn Asp Val
    50                  55                  60

Trp Glu Ala Phe Met Ala Gln Ile Glu Glu Leu Ile Glu Gln Arg Ile
65                  70                  75                  80

Ala Asp Gln Val Val Arg Asn Ala Leu Asp Asn Leu Thr Gly Leu Arg
                85                  90                  95

Asp Tyr Tyr Asn Gln Tyr Leu Leu Ala Leu Glu Glu Trp Gln Glu Arg
            100                 105                 110

Pro Asn Ala Val Arg Ser Thr Leu Val Phe Asn Arg Phe Glu Thr Leu
        115                 120                 125

His Ser His Phe Val Thr Ser Met Pro Ser Phe Gly Ser Gly Pro Gly
    130                 135                 140

Ser Glu Arg Tyr Ala Val Gln Leu Leu Thr Val Tyr Ala Gln Ala Ala
145                 150                 155                 160

Asn Leu His Leu Leu Leu Leu Arg Asp Ala Asp Ile Tyr Gly Ala Arg
                165                 170                 175

Trp Gly Leu Arg Glu Ser Gln Ile Asp Leu Tyr Phe Asn Glu Leu Gln
            180                 185                 190

Asn Arg Thr Arg Asp Tyr Thr Asn His Cys Val Thr Ala Tyr Asn Asn
        195                 200                 205

Gly Leu Glu Glu Ile Arg Gly Thr Ser Pro Ala Ser Trp Leu Arg Tyr
    210                 215                 220

His Gln Phe Arg Arg Glu Thr Thr Leu Ile Ala Leu Asp Leu Val Ala
225                 230                 235                 240

Ile Phe Pro Tyr Tyr Asn Val Arg Glu Tyr Pro Ile Gly Val Asn Pro
                245                 250                 255

Gln Leu Thr Arg Asp Val Tyr Thr Asp Pro Ile Gly Val Thr Phe Arg
            260                 265                 270

-continued

```
Arg Glu Asp Trp Glu Thr Gly Val Glu Cys Arg Pro Trp Val Asn Thr
            275                 280                 285

Pro Tyr Met Ser Phe Ser Asp Leu Glu Asn Ala Ile Ile Arg Pro Pro
        290                 295                 300

His Leu Phe Glu Thr Leu Arg Asn Leu Thr Ile His Thr Gly Arg Tyr
305                 310                 315                 320

Asn Leu Val Gly Gly Ala Arg Phe Ile Glu Gly Trp Val Gly His Ser
                325                 330                 335

Val Thr Asn Thr Arg Leu Gly Asn Ser Thr Val Phe Thr Ser Asn Tyr
            340                 345                 350

Gly Ser Leu Pro Pro Arg Phe Gln Val Phe Asn Phe Thr Asn Phe Asp
        355                 360                 365

Val Tyr Gln Ile Asn Thr Arg Ala Asp Ser Thr Gly Thr Phe Arg Ile
    370                 375                 380

Pro Gly Phe Ala Val Thr Arg Ala Gln Phe Ile Pro Gly Gly Thr Tyr
385                 390                 395                 400

Ser Val Ala His Arg Asp Pro Gly Ala Cys Gln Gln Asp Tyr Asp Ser
                405                 410                 415

Ile Glu Glu Leu Pro Ser Leu Asp Pro Asp Glu Pro Ile Asn Arg Ser
            420                 425                 430

Tyr Ser His Arg Leu Ser His Val Thr Leu Tyr Lys Tyr Thr Leu Ser
        435                 440                 445

Asp Thr Asp Tyr Gly Val Ile Asn Tyr Thr Asp Tyr Gly Ser Met Pro
    450                 455                 460

Ala Tyr Val Trp Thr His Arg Asp Val Asp Leu Thr Asn Thr Ile Thr
465                 470                 475                 480

Ala Asp Arg Ile Thr Gln Leu Pro Leu Val Lys Ala Ser Thr Leu Pro
                485                 490                 495

Ala Gly Thr Thr Val Val Lys Gly Pro Gly Phe Thr Gly Gly Asp Ile
            500                 505                 510

Leu Arg Arg Thr Thr Asn Gly Thr Phe Gly Thr Leu His Val Arg Val
        515                 520                 525

Asn Ser Pro Leu Thr Gln Gln Tyr Arg Leu Arg Val Arg Phe Ala Ser
    530                 535                 540

Thr Gly Asn Phe Ser Ile Arg Val Leu Arg Gly Gly Thr Ser Ile Gly
545                 550                 555                 560

Asp Ala Arg Phe Gly Ser Thr Met Asn Arg Gly Gln Glu Leu Thr Tyr
                565                 570                 575

Glu Ser Phe Val Thr Arg Glu Phe Thr Thr Thr Gly Pro Phe Asn Pro
            580                 585                 590

Pro Phe Thr Phe Thr Gln Thr Gln Glu Ile Leu Thr Val Asn Ala Glu
        595                 600                 605

Gly Val Ser Thr Gly Gly Glu Tyr Tyr Ile Asp Ser Ile Glu Ile Val
    610                 615                 620

Pro Val Asn Pro Thr Arg Glu Ala Glu Glu Asp Leu Glu Ala Ala Lys
625                 630                 635                 640

Lys Ala Val Ala Ser Leu Phe Thr Arg Thr Arg Asp Gly Leu Gln Val
                645                 650                 655

Asn Val Thr Asp Tyr Gln Val Asp Gln Ala Ala Asn Leu Val Ser Cys
            660                 665                 670

Leu Ser Asp Glu Gln Tyr Gly His Asp Lys Lys Met Leu Leu Glu Ala
        675                 680                 685

Val Arg Ala Ala Lys Arg Leu Ser Arg Glu Arg Asn Leu Leu Gln Asp
```

```
                690             695                 700
Pro Asp Phe Asn Thr Ile Asn Ser Thr Glu Glu Asn Gly Trp Lys Ala
705                     710                 715                 720

Ser Asn Gly Val Thr Ile Ser Glu Gly Gly Pro Phe Tyr Lys Gly Arg
                725                 730                 735

Ala Leu Gln Leu Ala Ser Ala Arg Glu Asn Tyr Pro Thr Tyr Ile Tyr
                740                 745                 750

Gln Lys Val Asn Ala Ser Glu Leu Lys Pro Tyr Thr Arg Tyr Arg Leu
        755                 760                 765

Asp Gly Phe Val Lys Ser Ser Gln Asp Leu Glu Ile Asp Leu Ile His
        770                 775                 780

His His Lys Val His Leu Val Lys Asn Val Pro Asp Asn Leu Val Ser
785                 790                 795                 800

Asp Thr Tyr Ser Asp Gly Ser Cys Ser Gly Met Asn Arg Cys Glu Glu
                805                 810                 815

Gln Gln Met Val Asn Ala Gln Leu Glu Thr Glu His His His Pro Met
                820                 825                 830

Asp Cys Cys Glu Ala Ala Gln Thr His Glu Phe Ser Ser Tyr Ile Asn
                835                 840                 845

Thr Gly Asp Leu Asn Ser Ser Val Asp Gln Gly Ile Trp Val Val Leu
                850                 855                 860

Lys Val Arg Thr Thr Asp Gly Tyr Ala Thr Leu Gly Asn Leu Glu Leu
865                 870                 875                 880

Val Glu Val Gly Pro Leu Ser Gly Glu Ser Leu Glu Arg Glu Gln Arg
                885                 890                 895

Asp Asn Ala Lys Trp Ser Ala Glu Leu Gly Arg Lys Arg Ala Glu Thr
                900                 905                 910

Asp Arg Val Tyr Gln Asp Ala Lys Gln Ser Ile Asn His Leu Phe Val
                915                 920                 925

Asp Tyr Gln Asp Gln Gln Leu Asn Pro Glu Ile Gly Met Ala Asp Ile
                930                 935                 940

Ile Asp Ala Gln Asn Leu Val Ala Ser Ile Ser Asp Val Tyr Ser Asp
945                 950                 955                 960

Ala Val Leu Gln Ile Pro Gly Ile Asn Tyr Glu Ile Tyr Thr Glu Leu
                965                 970                 975

Ser Asn Arg Leu Gln Gln Ala Ser Tyr Leu Tyr Thr Ser Arg Asn Ala
                980                 985                 990

Val Gln Asn Gly Asp Phe Asn Ser Gly Leu Asp Ser Trp Asn Ala Thr
                995                 1000                1005

Gly Gly Ala Thr Val Gln Gln Asp Gly Asn Thr His Phe Leu Val
        1010                1015                1020

Leu Ser His Trp Asp Ala Gln Val Ser Gln Gln Phe Arg Val Gln
        1025                1030                1035

Pro Asn Cys Lys Tyr Val Leu Arg Val Thr Ala Glu Lys Val Gly
        1040                1045                1050

Gly Gly Asp Gly Tyr Val Thr Ile Arg Asp Gly Ala His His Thr
        1055                1060                1065

Glu Lys Leu Thr Phe Asn Ala Cys Asp Tyr Asp Ile Asn Gly Thr
        1070                1075                1080

Tyr Val Thr Asp Asn Thr Tyr Leu Thr Lys Glu Val Val Phe Tyr
        1085                1090                1095

Ser His Thr Glu His Met Trp Val Glu Val Ser Glu Thr Glu Gly
        1100                1105                1110
```

```
Ala Phe  His Ile Asp Ser Ile  Glu Phe Val Glu Thr  Glu Lys
    1115                 1120                1125

<210> SEQ ID NO 8
<211> LENGTH: 673
<212> TYPE: PRT
<213> ORGANISM: Bacillus thuringiensis

<400> SEQUENCE: 8

Met Asn Arg Asn Asn Gln Gly Glu Tyr Glu Ile Ile Asp Ala Ser Thr
1               5                   10                  15

Cys Gly Cys Ser Ser Asp Asp Val Val Gln Tyr Pro Leu Ala Arg Asp
            20                  25                  30

Pro Asn Ala Ala Phe Gln Asn Met Asn Tyr Lys Asp Tyr Leu Lys Met
        35                  40                  45

Ser Asp Gly Asp Tyr Val Asp Ser Tyr Ile Asn Pro Gly Leu Ser Ile
    50                  55                  60

Gly Arg Arg Asp Val Thr Leu Thr Gly Val Gly Ile Val Ala Leu Ile
65                  70                  75                  80

Val Gly Thr Leu Gly Gly Pro Val Gly Gly Ile Val Thr Gly Leu Ile
                85                  90                  95

Ser Ser Leu Leu Gly Leu Leu Trp Pro Ser Asn Asp Asn Asp Val Trp
            100                 105                 110

Glu Ala Phe Met Ala Gln Ile Glu Glu Leu Ile Glu Gln Arg Ile Ala
        115                 120                 125

Asp Gln Val Val Arg Asn Ala Leu Asp Asn Leu Thr Gly Leu Arg Asp
    130                 135                 140

Tyr Tyr Asn Gln Tyr Leu Leu Ala Leu Glu Glu Trp Gln Glu Arg Pro
145                 150                 155                 160

Asn Ala Val Arg Ser Thr Leu Val Phe Asn Arg Phe Glu Thr Leu His
                165                 170                 175

Ser His Phe Val Thr Ser Met Pro Ser Phe Gly Ser Gly Pro Gly Ser
            180                 185                 190

Glu Arg Tyr Ala Val Gln Leu Leu Thr Val Tyr Ala Gln Ala Ala Asn
        195                 200                 205

Leu His Leu Leu Leu Leu Arg Asp Ala Asp Ile Tyr Gly Ala Arg Trp
    210                 215                 220

Gly Leu Arg Glu Ser Gln Ile Asp Leu Tyr Phe Asn Glu Leu Gln Asn
225                 230                 235                 240

Arg Thr Arg Asp Tyr Thr Asn His Cys Val Thr Ala Tyr Asn Asn Gly
                245                 250                 255

Leu Glu Glu Ile Arg Gly Thr Ser Pro Ala Ser Trp Leu Arg Tyr His
            260                 265                 270

Gln Phe Arg Arg Glu Thr Thr Leu Ile Ala Leu Asp Leu Val Ala Ile
        275                 280                 285

Phe Pro Tyr Tyr Asn Val Arg Glu Tyr Pro Ile Gly Val Asn Pro Gln
    290                 295                 300

Leu Thr Arg Asp Val Tyr Thr Asp Pro Ile Gly Val Thr Phe Arg Arg
305                 310                 315                 320

Glu Asp Trp Glu Thr Gly Val Glu Cys Arg Pro Trp Val Asn Thr Pro
                325                 330                 335

Tyr Met Ser Phe Ser Asp Leu Glu Asn Ala Ile Ile Arg Pro Pro His
            340                 345                 350

Leu Phe Glu Thr Leu Arg Asn Leu Thr Ile His Thr Gly Arg Tyr Asn
```

```
              355                 360                 365
Leu Val Gly Gly Ala Arg Phe Ile Glu Gly Trp Val Gly His Ser Val
370                 375                 380

Thr Asn Thr Arg Leu Gly Asn Ser Thr Val Phe Thr Ser Asn Tyr Gly
385                 390                 395                 400

Ser Leu Pro Pro Arg Phe Gln Val Phe Asn Phe Thr Asn Phe Asp Val
                405                 410                 415

Tyr Gln Ile Asn Thr Arg Ala Asp Ser Thr Gly Thr Phe Arg Ile Pro
            420                 425                 430

Gly Phe Ala Val Thr Arg Ala Gln Phe Ile Pro Gly Gly Thr Tyr Ser
        435                 440                 445

Val Ala His Arg Asp Pro Gly Ala Cys Gln Gln Asp Tyr Asp Ser Ile
    450                 455                 460

Glu Glu Leu Pro Ser Leu Asp Pro Asp Glu Pro Ile Asn Arg Ser Tyr
465                 470                 475                 480

Ser His Arg Leu Ser His Val Thr Leu Tyr Lys Tyr Thr Leu Ser Asp
                485                 490                 495

Thr Asp Tyr Gly Val Ile Asn Tyr Thr Asp Tyr Gly Ser Met Pro Ala
            500                 505                 510

Tyr Val Trp Thr His Arg Asp Val Asp Leu Thr Asn Thr Ile Thr Ala
        515                 520                 525

Asp Arg Ile Thr Gln Leu Pro Leu Val Lys Ala Ser Thr Leu Pro Ala
    530                 535                 540

Gly Thr Thr Val Val Lys Gly Pro Gly Phe Thr Gly Gly Asp Ile Leu
545                 550                 555                 560

Arg Arg Thr Thr Asn Gly Thr Phe Gly Thr Leu His Val Arg Val Asn
                565                 570                 575

Ser Pro Leu Thr Gln Gln Tyr Arg Leu Arg Val Arg Phe Ala Ser Thr
            580                 585                 590

Gly Asn Phe Ser Ile Arg Val Leu Arg Gly Gly Thr Ser Ile Gly Asp
        595                 600                 605

Ala Arg Phe Gly Ser Thr Met Asn Arg Gly Gln Glu Leu Thr Tyr Glu
    610                 615                 620

Ser Phe Val Thr Arg Glu Phe Thr Thr Thr Gly Pro Phe Asn Pro Pro
625                 630                 635                 640

Phe Thr Phe Thr Gln Thr Gln Glu Ile Leu Thr Val Asn Ala Glu Gly
                645                 650                 655

Val Ser Thr Gly Gly Glu Tyr Tyr Ile Asp Ser Ile Glu Ile Val Pro
            660                 665                 670

Val

<210> SEQ ID NO 9
<211> LENGTH: 634
<212> TYPE: PRT
<213> ORGANISM: Bacillus thuringiensis

<400> SEQUENCE: 9

Met Asn Tyr Lys Asp Tyr Leu Lys Met Ser Asp Gly Asp Tyr Val Asp
1               5                   10                  15

Ser Tyr Ile Asn Pro Gly Leu Ser Ile Gly Arg Arg Asp Val Thr Leu
            20                  25                  30

Thr Gly Val Gly Ile Val Ala Leu Ile Val Gly Thr Leu Gly Gly Pro
        35                  40                  45

Val Gly Gly Ile Val Thr Gly Leu Ile Ser Ser Leu Leu Gly Leu Leu
```

-continued

```
                50                  55                  60
Trp Pro Ser Asn Asp Asn Asp Val Trp Glu Ala Phe Met Ala Gln Ile
 65                  70                  75                  80

Glu Glu Leu Ile Glu Gln Arg Ile Ala Asp Gln Val Val Arg Asn Ala
                 85                  90                  95

Leu Asp Asn Leu Thr Gly Leu Arg Asp Tyr Tyr Asn Gln Tyr Leu Leu
                100                 105                 110

Ala Leu Glu Glu Trp Gln Glu Arg Pro Asn Ala Val Arg Ser Thr Leu
                115                 120                 125

Val Phe Asn Arg Phe Glu Thr Leu His Ser His Phe Val Thr Ser Met
130                 135                 140

Pro Ser Phe Gly Ser Gly Pro Gly Ser Glu Arg Tyr Ala Val Gln Leu
145                 150                 155                 160

Leu Thr Val Tyr Ala Gln Ala Ala Asn Leu His Leu Leu Leu Leu Arg
                165                 170                 175

Asp Ala Asp Ile Tyr Gly Ala Arg Trp Gly Leu Arg Glu Ser Gln Ile
                180                 185                 190

Asp Leu Tyr Phe Asn Glu Leu Gln Asn Arg Thr Arg Asp Tyr Thr Asn
                195                 200                 205

His Cys Val Thr Ala Tyr Asn Asn Gly Leu Glu Glu Ile Arg Gly Thr
                210                 215                 220

Ser Pro Ala Ser Trp Leu Arg Tyr His Gln Phe Arg Arg Glu Thr Thr
225                 230                 235                 240

Leu Ile Ala Leu Asp Leu Val Ala Ile Phe Pro Tyr Tyr Asn Val Arg
                245                 250                 255

Glu Tyr Pro Ile Gly Val Asn Pro Gln Leu Thr Arg Asp Val Tyr Thr
                260                 265                 270

Asp Pro Ile Gly Val Thr Phe Arg Arg Glu Asp Trp Glu Thr Gly Val
                275                 280                 285

Glu Cys Arg Pro Trp Val Asn Thr Pro Tyr Met Ser Phe Ser Asp Leu
                290                 295                 300

Glu Asn Ala Ile Ile Arg Pro Pro His Leu Phe Glu Thr Leu Arg Asn
305                 310                 315                 320

Leu Thr Ile His Thr Gly Arg Tyr Asn Leu Val Gly Gly Ala Arg Phe
                325                 330                 335

Ile Glu Gly Trp Val Gly His Ser Val Thr Asn Thr Arg Leu Gly Asn
                340                 345                 350

Ser Thr Val Phe Thr Ser Asn Tyr Gly Ser Leu Pro Pro Arg Phe Gln
                355                 360                 365

Val Phe Asn Phe Thr Asn Phe Asp Val Tyr Gln Ile Asn Thr Arg Ala
                370                 375                 380

Asp Ser Thr Gly Thr Phe Arg Ile Pro Gly Phe Ala Val Thr Arg Ala
385                 390                 395                 400

Gln Phe Ile Pro Gly Gly Thr Tyr Ser Val Ala His Arg Asp Pro Gly
                405                 410                 415

Ala Cys Gln Gln Asp Tyr Asp Ser Ile Glu Glu Leu Pro Ser Leu Asp
                420                 425                 430

Pro Asp Glu Pro Ile Asn Arg Ser Tyr Ser His Arg Leu Ser His Val
                435                 440                 445

Thr Leu Tyr Lys Tyr Thr Leu Ser Asp Thr Asp Tyr Gly Val Ile Asn
                450                 455                 460

Tyr Thr Asp Tyr Gly Ser Met Pro Ala Tyr Val Trp Thr His Arg Asp
465                 470                 475                 480
```

-continued

Val Asp Leu Thr Asn Thr Ile Thr Ala Asp Arg Ile Thr Gln Leu Pro
            485                 490                 495

Leu Val Lys Ala Ser Thr Leu Pro Ala Gly Thr Val Val Lys Gly
        500                 505                 510

Pro Gly Phe Thr Gly Gly Asp Ile Leu Arg Arg Thr Asn Gly Thr
        515                 520                 525

Phe Gly Thr Leu His Val Arg Val Asn Ser Pro Leu Thr Gln Gln Tyr
        530                 535                 540

Arg Leu Arg Val Arg Phe Ala Ser Thr Gly Asn Phe Ser Ile Arg Val
545                 550                 555                 560

Leu Arg Gly Gly Thr Ser Ile Gly Asp Ala Arg Phe Gly Ser Thr Met
                565                 570                 575

Asn Arg Gly Gln Glu Leu Thr Tyr Glu Ser Phe Val Thr Arg Glu Phe
                580                 585                 590

Thr Thr Thr Gly Pro Phe Asn Pro Pro Phe Thr Phe Thr Gln Thr Gln
                595                 600                 605

Glu Ile Leu Thr Val Asn Ala Glu Gly Val Ser Thr Gly Gly Glu Tyr
            610                 615                 620

Tyr Ile Asp Ser Ile Glu Ile Val Pro Val
625                 630

<210> SEQ ID NO 10
<211> LENGTH: 626
<212> TYPE: PRT
<213> ORGANISM: Bacillus thuringiensis

<400> SEQUENCE: 10

Met Ser Asp Gly Asp Tyr Val Asp Ser Tyr Ile Asn Pro Gly Leu Ser
1               5                   10                  15

Ile Gly Arg Arg Asp Val Thr Leu Thr Gly Val Gly Ile Val Ala Leu
            20                  25                  30

Ile Val Gly Thr Leu Gly Gly Pro Val Gly Gly Ile Val Thr Gly Leu
        35                  40                  45

Ile Ser Ser Leu Leu Gly Leu Leu Trp Pro Ser Asn Asp Asn Asp Val
    50                  55                  60

Trp Glu Ala Phe Met Ala Gln Ile Glu Glu Leu Ile Glu Gln Arg Ile
65                  70                  75                  80

Ala Asp Gln Val Val Arg Asn Ala Leu Asp Asn Leu Thr Gly Leu Arg
                85                  90                  95

Asp Tyr Tyr Asn Gln Tyr Leu Leu Ala Leu Glu Glu Trp Gln Glu Arg
            100                 105                 110

Pro Asn Ala Val Arg Ser Thr Leu Val Phe Asn Arg Phe Glu Thr Leu
        115                 120                 125

His Ser His Phe Val Thr Ser Met Pro Ser Phe Gly Ser Gly Pro Gly
    130                 135                 140

Ser Glu Arg Tyr Ala Val Gln Leu Leu Thr Val Tyr Ala Gln Ala Ala
145                 150                 155                 160

Asn Leu His Leu Leu Leu Leu Arg Asp Ala Asp Ile Tyr Gly Ala Arg
                165                 170                 175

Trp Gly Leu Arg Glu Ser Gln Ile Asp Leu Tyr Phe Asn Glu Leu Gln
            180                 185                 190

Asn Arg Thr Arg Asp Tyr Thr Asn His Cys Val Thr Ala Tyr Asn Asn
        195                 200                 205

Gly Leu Glu Glu Ile Arg Gly Thr Ser Pro Ala Ser Trp Leu Arg Tyr

```
            210                 215                 220
His Gln Phe Arg Arg Glu Thr Thr Leu Ile Ala Leu Asp Leu Val Ala
225                 230                 235                 240

Ile Phe Pro Tyr Tyr Asn Val Arg Glu Tyr Pro Ile Gly Val Asn Pro
                245                 250                 255

Gln Leu Thr Arg Asp Val Tyr Thr Asp Pro Ile Gly Val Thr Phe Arg
                260                 265                 270

Arg Glu Asp Trp Glu Thr Gly Val Glu Cys Arg Pro Trp Val Asn Thr
            275                 280                 285

Pro Tyr Met Ser Phe Ser Asp Leu Glu Asn Ala Ile Ile Arg Pro Pro
            290                 295                 300

His Leu Phe Glu Thr Leu Arg Asn Leu Thr Ile His Thr Gly Arg Tyr
305                 310                 315                 320

Asn Leu Val Gly Gly Ala Arg Phe Ile Glu Gly Trp Val Gly His Ser
                325                 330                 335

Val Thr Asn Thr Arg Leu Gly Asn Ser Thr Val Phe Thr Ser Asn Tyr
                340                 345                 350

Gly Ser Leu Pro Pro Arg Phe Gln Val Phe Asn Phe Thr Asn Phe Asp
            355                 360                 365

Val Tyr Gln Ile Asn Thr Arg Ala Asp Ser Thr Gly Thr Phe Arg Ile
            370                 375                 380

Pro Gly Phe Ala Val Thr Arg Ala Gln Phe Ile Pro Gly Gly Thr Tyr
385                 390                 395                 400

Ser Val Ala His Arg Asp Pro Gly Ala Cys Gln Gln Asp Tyr Asp Ser
                405                 410                 415

Ile Glu Glu Leu Pro Ser Leu Asp Pro Asp Glu Pro Ile Asn Arg Ser
                420                 425                 430

Tyr Ser His Arg Leu Ser His Val Thr Leu Tyr Lys Tyr Thr Leu Ser
            435                 440                 445

Asp Thr Asp Tyr Gly Val Ile Asn Tyr Thr Asp Tyr Gly Ser Met Pro
450                 455                 460

Ala Tyr Val Trp Thr His Arg Asp Val Asp Leu Thr Asn Thr Ile Thr
465                 470                 475                 480

Ala Asp Arg Ile Thr Gln Leu Pro Leu Val Lys Ala Ser Thr Leu Pro
                485                 490                 495

Ala Gly Thr Thr Val Val Lys Gly Pro Gly Phe Thr Gly Gly Asp Ile
                500                 505                 510

Leu Arg Arg Thr Thr Asn Gly Thr Phe Gly Thr Leu His Val Arg Val
            515                 520                 525

Asn Ser Pro Leu Thr Gln Gln Tyr Arg Leu Arg Val Arg Phe Ala Ser
530                 535                 540

Thr Gly Asn Phe Ser Ile Arg Val Leu Arg Gly Gly Thr Ser Ile Gly
545                 550                 555                 560

Asp Ala Arg Phe Gly Ser Thr Met Asn Arg Gly Gln Glu Leu Thr Tyr
                565                 570                 575

Glu Ser Phe Val Thr Arg Glu Phe Thr Thr Gly Pro Phe Asn Pro
                580                 585                 590

Pro Phe Thr Phe Thr Gln Thr Gln Glu Ile Leu Thr Val Asn Ala Glu
            595                 600                 605

Gly Val Ser Thr Gly Gly Glu Tyr Tyr Ile Asp Ser Ile Glu Ile Val
        610                 615                 620

Pro Val
625
```

<210> SEQ ID NO 11
<211> LENGTH: 336
<212> TYPE: PRT
<213> ORGANISM: Bacillus thuringiensis

<400> SEQUENCE: 11

```
Met Asn Lys Lys Val Thr Lys Thr Val Leu Ser Val Met Gly Ile
1               5                   10                  15

Ser Val Leu Ala Ser Pro Leu Ala Val Ala Lys Thr Glu Asn Asn
                20                  25                  30

Lys Glu Gln Gln Val Ile Thr Gln Phe Asn Gln Arg Glu Asn Lys Phe
                35                  40                  45

Pro Asp Val Gly Gln Gly Ile Gln Trp Leu Ser Gln Phe Tyr Gly Lys
50                  55                  60

Ser Leu Lys Asn Asn Gly Glu Gly Tyr Ser Leu Gly Asn Asp Val Met
65                  70                  75                  80

Ser Tyr Phe Leu Glu Val Lys Asn Ser Tyr Gln Leu Ala Ile Glu
                85                  90                  95

Pro Gln Val Ile Ser Thr Thr Pro Leu Trp Ala Gly Gln Ser Asp Leu
                100                 105                 110

Glu Asn Ala Thr Asp His Glu Gln Thr Leu Asn Ser Thr Glu Phe Lys
                115                 120                 125

Lys Thr Tyr Ser Asn Thr Thr Thr Ser Thr Glu Asn Gly Phe Met
                130                 135                 140

Ile Gly Gln Glu Thr Glu Gly Lys Val Gly Ile Pro Phe Val Ala Glu
145                 150                 155                 160

Gly Lys Val Thr Ile Lys Thr Glu Tyr Asn Phe Asn His Thr Asn Gly
                165                 170                 175

Tyr Glu Thr Ser Glu Ser Val Glu Tyr Ile Ala Pro Ser Gln Ser Ile
                180                 185                 190

Lys Val Pro Pro His Thr Ile Ala Arg Val Thr Ala Leu Leu Asp Val
                195                 200                 205

Lys Lys Ile Lys Gly Lys Met His Leu Tyr Ser Glu Ile Gly Leu Asn
210                 215                 220

Lys Asp Tyr Gly Tyr Asp Met Val Pro Leu Val Tyr Lys Tyr Gly Gly
225                 230                 235                 240

Pro Phe Lys Tyr Val Thr Leu Gly Thr Leu Tyr Asp Glu Gly Tyr Lys
                245                 250                 255

Gln Ala Gln Leu Asp Tyr Ser Asn Met Gly Asn Val Ile Pro Glu Glu
                260                 265                 270

Ile Glu Thr Val Ser Lys Ser Asn Asn Pro Asn His Leu Leu Ala Ser
                275                 280                 285

Gly Leu Gly Ile Phe Glu Ser Glu Tyr Gly Ser Val Phe Asn Val Lys
                290                 295                 300

Val Glu Tyr Ile Asn Ile Lys Thr Lys Lys Ile Glu Lys Thr Glu Asn
305                 310                 315                 320

Leu Thr Ile Glu Pro Thr Ile Val Pro Val Glu Lys Thr Asn Thr Lys
                325                 330                 335
```

<210> SEQ ID NO 12
<211> LENGTH: 323
<212> TYPE: PRT
<213> ORGANISM: Bacillus thuringiensis

<400> SEQUENCE: 12

```
Met Gly Ile Ser Val Leu Ala Ser Pro Leu Ala Val Ala Ala Lys Thr
1               5                   10                  15

Glu Asn Asn Lys Glu Gln Gln Val Ile Thr Gln Phe Asn Gln Arg Glu
            20                  25                  30

Asn Lys Phe Pro Asp Val Gly Gln Gly Ile Gln Trp Leu Ser Gln Phe
        35                  40                  45

Tyr Gly Lys Ser Leu Lys Asn Asn Gly Glu Gly Tyr Ser Leu Gly Asn
    50                  55                  60

Asp Val Met Ser Tyr Phe Leu Glu Val Lys Asn Ser Tyr Gly Gln Leu
65                  70                  75                  80

Ala Ile Glu Pro Gln Val Ile Ser Thr Thr Pro Leu Trp Ala Gly Gln
                85                  90                  95

Ser Asp Leu Glu Asn Ala Thr Asp His Glu Gln Thr Leu Asn Ser Thr
            100                 105                 110

Glu Phe Lys Lys Thr Tyr Ser Asn Thr Thr Thr Thr Ser Thr Glu Asn
        115                 120                 125

Gly Phe Met Ile Gly Gln Glu Thr Glu Gly Lys Val Gly Ile Pro Phe
    130                 135                 140

Val Ala Glu Gly Lys Val Thr Ile Lys Thr Glu Tyr Asn Phe Asn His
145                 150                 155                 160

Thr Asn Gly Tyr Glu Thr Ser Glu Ser Val Glu Tyr Ile Ala Pro Ser
                165                 170                 175

Gln Ser Ile Lys Val Pro Pro His Thr Ile Ala Arg Val Thr Ala Leu
            180                 185                 190

Leu Asp Val Lys Lys Ile Lys Gly Lys Met His Leu Tyr Ser Glu Ile
        195                 200                 205

Gly Leu Asn Lys Asp Tyr Gly Tyr Asp Met Val Pro Leu Val Tyr Lys
    210                 215                 220

Tyr Gly Gly Pro Phe Lys Tyr Val Thr Leu Gly Thr Leu Tyr Asp Glu
225                 230                 235                 240

Gly Tyr Lys Gln Ala Gln Leu Asp Tyr Ser Asn Met Gly Asn Val Ile
                245                 250                 255

Pro Glu Glu Ile Glu Thr Val Ser Lys Ser Asn Asn Pro Asn His Leu
            260                 265                 270

Leu Ala Ser Gly Leu Gly Ile Phe Glu Ser Glu Tyr Gly Ser Val Phe
        275                 280                 285

Asn Val Lys Val Glu Tyr Ile Asn Ile Lys Thr Lys Lys Ile Glu Lys
    290                 295                 300

Thr Glu Asn Leu Thr Ile Glu Pro Thr Ile Val Pro Val Glu Lys Thr
305                 310                 315                 320

Asn Thr Lys
```

<210> SEQ ID NO 13
<211> LENGTH: 310
<212> TYPE: PRT
<213> ORGANISM: Bacillus thuringiensis

<400> SEQUENCE: 13

```
Met Lys Thr Glu Asn Asn Lys Glu Gln Gln Val Ile Thr Gln Phe Asn
1               5                   10                  15

Gln Arg Glu Asn Lys Phe Pro Asp Val Gly Gln Gly Ile Gln Trp Leu
            20                  25                  30

Ser Gln Phe Tyr Gly Lys Ser Leu Lys Asn Asn Gly Glu Gly Tyr Ser
        35                  40                  45
```

```
Leu Gly Asn Asp Val Met Ser Tyr Phe Leu Glu Val Lys Asn Ser Tyr
 50                  55                  60

Gly Gln Leu Ala Ile Glu Pro Gln Val Ile Ser Thr Thr Pro Leu Trp
 65                  70                  75                  80

Ala Gly Gln Ser Asp Leu Glu Asn Ala Thr Asp His Glu Gln Thr Leu
                 85                  90                  95

Asn Ser Thr Glu Phe Lys Lys Thr Tyr Ser Asn Thr Thr Thr Thr Ser
            100                 105                 110

Thr Glu Asn Gly Phe Met Ile Gly Gln Glu Thr Glu Gly Lys Val Gly
            115                 120                 125

Ile Pro Phe Val Ala Glu Gly Lys Val Thr Ile Lys Thr Glu Tyr Asn
            130                 135                 140

Phe Asn His Thr Asn Gly Tyr Glu Thr Ser Glu Ser Val Glu Tyr Ile
145                 150                 155                 160

Ala Pro Ser Gln Ser Ile Lys Val Pro Pro His Thr Ile Ala Arg Val
                165                 170                 175

Thr Ala Leu Leu Asp Val Lys Lys Ile Lys Gly Lys Met His Leu Tyr
            180                 185                 190

Ser Glu Ile Gly Leu Asn Lys Asp Tyr Gly Tyr Asp Met Val Pro Leu
            195                 200                 205

Val Tyr Lys Tyr Gly Gly Pro Phe Lys Tyr Val Thr Leu Gly Thr Leu
            210                 215                 220

Tyr Asp Glu Gly Tyr Lys Gln Ala Gln Leu Asp Tyr Ser Asn Met Gly
225                 230                 235                 240

Asn Val Ile Pro Glu Glu Ile Glu Thr Val Ser Lys Ser Asn Asn Pro
                245                 250                 255

Asn His Leu Leu Ala Ser Gly Leu Gly Ile Phe Glu Ser Glu Tyr Gly
            260                 265                 270

Ser Val Phe Asn Val Lys Val Glu Tyr Ile Asn Ile Lys Thr Lys Lys
            275                 280                 285

Ile Glu Lys Thr Glu Asn Leu Thr Ile Glu Pro Thr Ile Val Pro Val
            290                 295                 300

Glu Lys Thr Asn Thr Lys
305                 310

<210> SEQ ID NO 14
<211> LENGTH: 257
<212> TYPE: PRT
<213> ORGANISM: Bacillus thuringiensis

<400> SEQUENCE: 14

Met Ser Tyr Phe Leu Glu Val Lys Asn Ser Tyr Gly Gln Leu Ala Ile
 1               5                  10                  15

Glu Pro Gln Val Ile Ser Thr Thr Pro Leu Trp Ala Gly Gln Ser Asp
                20                  25                  30

Leu Glu Asn Ala Thr Asp His Glu Gln Thr Leu Asn Ser Thr Glu Phe
             35                  40                  45

Lys Lys Thr Tyr Ser Asn Thr Thr Thr Thr Ser Thr Glu Asn Gly Phe
 50                  55                  60

Met Ile Gly Gln Glu Thr Glu Gly Lys Val Gly Ile Pro Phe Val Ala
 65                  70                  75                  80

Glu Gly Lys Val Thr Ile Lys Thr Glu Tyr Asn Phe Asn His Thr Asn
                 85                  90                  95

Gly Tyr Glu Thr Ser Glu Ser Val Glu Tyr Ile Ala Pro Ser Gln Ser
```

```
                        100                 105                 110
        Ile Lys Val Pro Pro His Thr Ile Ala Arg Val Thr Ala Leu Leu Asp
                    115                 120                 125

Val Lys Lys Ile Lys Gly Lys Met His Leu Tyr Ser Glu Ile Gly Leu
                    130                 135                 140

Asn Lys Asp Tyr Gly Tyr Asp Met Val Pro Leu Val Tyr Lys Tyr Gly
        145                 150                 155                 160

Gly Pro Phe Lys Tyr Val Thr Leu Gly Thr Leu Tyr Asp Glu Gly Tyr
                            165                 170                 175

Lys Gln Ala Gln Leu Asp Tyr Ser Asn Met Gly Asn Val Ile Pro Glu
                        180                 185                 190

Glu Ile Glu Thr Val Ser Lys Ser Asn Asn Pro Asn His Leu Leu Ala
                    195                 200                 205

Ser Gly Leu Gly Ile Phe Glu Ser Glu Tyr Gly Ser Val Phe Asn Val
                    210                 215                 220

Lys Val Glu Tyr Ile Asn Ile Lys Thr Lys Lys Ile Glu Lys Thr Glu
        225                 230                 235                 240

Asn Leu Thr Ile Glu Pro Thr Ile Val Pro Val Glu Lys Thr Asn Thr
                            245                 250                 255

Lys

<210> SEQ ID NO 15
<211> LENGTH: 341
<212> TYPE: PRT
<213> ORGANISM: Bacillus thuringiensis

<400> SEQUENCE: 15

Met Arg Glu Lys Asp Leu Asn Lys Lys Val Thr Lys Ala Val Leu Ser
        1               5                   10                  15

Met Ile Val Gly Ile Ser Val Leu Ala Ser Pro Leu Ala Val Ala Ala
                        20                  25                  30

Lys Thr Glu Asn Asn Lys Glu Gln Gln Val Ile Thr His Phe Asn Gln
                    35                  40                  45

Arg Glu Asn Lys Phe Pro Asp Val Gly Gln Gly Ile Gln Trp Leu Ser
                50                  55                  60

Gln Phe Tyr Gly Lys Ser Leu Lys Asn Asn Gly Glu Gly Tyr Ser Leu
        65                  70                  75                  80

Gly Gln Asp Val Met Arg Tyr Phe Leu Glu Val Lys Asn Ser Tyr Gly
                        85                  90                  95

Gln Leu Ala Met Glu Pro Gln Val Ile Ser Thr Thr Pro Leu Trp Ala
                    100                 105                 110

Gly Gln Ser Asp Leu Glu Asn Ala Thr Asp His Glu Gln Thr Leu Asn
                    115                 120                 125

Ser Thr Glu Phe Lys Lys Thr Tyr Ser Asn Thr Thr Thr Ser Thr
                    130                 135                 140

Glu Asn Gly Phe Met Ile Gly Gln Glu Thr Gly Lys Val Gly Ile
        145                 150                 155                 160

Pro Phe Val Ala Glu Gly Lys Val Thr Ile Lys Thr Glu Tyr Asn Phe
                            165                 170                 175

Asn His Thr Asn Gly Tyr Glu Thr Ser Glu Ser Val Glu Tyr Ile Ala
                        180                 185                 190

Pro Ser Gln Ser Ile Lys Val Pro Pro His Thr Ile Ala Arg Val Thr
                    195                 200                 205

Ala Leu Leu Asp Val Lys Lys Ile Lys Gly Lys Met His Leu Tyr Ser
```

```
                210                 215                 220
Glu Ile Gly Leu Asn Lys Asp Tyr Gly Tyr Asp Met Val Pro Leu Val
225                 230                 235                 240

Tyr Lys Tyr Gly Gly Pro Phe Lys Tyr Val Thr Leu Gly Thr Leu Tyr
                245                 250                 255

Asp Glu Gly Tyr Lys Gln Ala Gln Leu Asp Tyr Phe Asn Met Gly Asn
                260                 265                 270

Val Ile Pro Glu Glu Ile Glu Thr Val Ser Lys Ser Asn Asn Pro Asn
            275                 280                 285

His Leu Leu Ala Ser Gly Val Gly Ile Phe Glu Ser Glu Tyr Gly Ser
        290                 295                 300

Val Phe Asn Val Lys Val Glu Tyr Ile Asn Ile Asn Thr Lys Lys Ile
305                 310                 315                 320

Glu Lys Thr Glu Asn Leu Thr Ile Glu Pro Thr Ile Val Pro Val Lys
                325                 330                 335

Gln Thr Asn Thr Lys
                340
```

<210> SEQ ID NO 16
<211> LENGTH: 325
<212> TYPE: PRT
<213> ORGANISM: Bacillus thuringiensis

<400> SEQUENCE: 16

```
Met Ile Val Gly Ile Ser Val Leu Ala Ser Pro Leu Ala Val Ala Ala
1               5                   10                  15

Lys Thr Glu Asn Asn Lys Glu Gln Gln Val Ile Thr His Phe Asn Gln
                20                  25                  30

Arg Glu Asn Lys Phe Pro Asp Val Gly Gln Gly Ile Gln Trp Leu Ser
            35                  40                  45

Gln Phe Tyr Gly Lys Ser Leu Lys Asn Asn Gly Glu Gly Tyr Ser Leu
        50                  55                  60

Gly Gln Asp Val Met Arg Tyr Phe Leu Glu Val Lys Asn Ser Tyr Gly
65                  70                  75                  80

Gln Leu Ala Met Glu Pro Gln Val Ile Ser Thr Thr Pro Leu Trp Ala
                85                  90                  95

Gly Gln Ser Asp Leu Glu Asn Ala Thr Asp His Glu Gln Thr Leu Asn
            100                 105                 110

Ser Thr Glu Phe Lys Lys Thr Tyr Ser Asn Thr Thr Thr Ser Thr
        115                 120                 125

Glu Asn Gly Phe Met Ile Gly Gln Thr Glu Gly Lys Val Gly Ile
    130                 135                 140

Pro Phe Val Ala Glu Gly Lys Val Thr Ile Lys Thr Glu Tyr Asn Phe
145                 150                 155                 160

Asn His Thr Asn Gly Tyr Glu Thr Ser Glu Ser Val Glu Tyr Ile Ala
                165                 170                 175

Pro Ser Gln Ser Ile Lys Val Pro Pro His Thr Ile Ala Arg Val Thr
            180                 185                 190

Ala Leu Leu Asp Val Lys Lys Ile Lys Gly Lys Met His Leu Tyr Ser
        195                 200                 205

Glu Ile Gly Leu Asn Lys Asp Tyr Gly Tyr Asp Met Val Pro Leu Val
    210                 215                 220

Tyr Lys Tyr Gly Gly Pro Phe Lys Tyr Val Thr Leu Gly Thr Leu Tyr
225                 230                 235                 240
```

```
Asp Glu Gly Tyr Lys Gln Ala Gln Leu Asp Tyr Phe Asn Met Gly Asn
                245                 250                 255

Val Ile Pro Glu Glu Ile Glu Thr Val Ser Lys Ser Asn Asn Pro Asn
            260                 265                 270

His Leu Leu Ala Ser Gly Val Gly Ile Phe Glu Ser Glu Tyr Gly Ser
        275                 280                 285

Val Phe Asn Val Lys Val Glu Tyr Ile Asn Ile Asn Thr Lys Lys Ile
290                 295                 300

Glu Lys Thr Glu Asn Leu Thr Ile Glu Pro Thr Ile Val Pro Val Lys
305                 310                 315                 320

Gln Thr Asn Thr Lys
            325

<210> SEQ ID NO 17
<211> LENGTH: 315
<212> TYPE: PRT
<213> ORGANISM: Bacillus thuringiensis

<400> SEQUENCE: 17

Met Leu Ala Val Ala Ala Lys Thr Glu Asn Asn Lys Glu Gln Gln Val
1               5                   10                  15

Ile Thr His Phe Asn Gln Arg Glu Asn Lys Phe Pro Asp Val Gly Gln
            20                  25                  30

Gly Ile Gln Trp Leu Ser Gln Phe Tyr Gly Lys Ser Leu Lys Asn Asn
        35                  40                  45

Gly Glu Gly Tyr Ser Leu Gly Gln Asp Val Met Arg Tyr Phe Leu Glu
    50                  55                  60

Val Lys Asn Ser Tyr Gly Gln Leu Ala Met Glu Pro Gln Val Ile Ser
65                  70                  75                  80

Thr Thr Pro Leu Trp Ala Gly Gln Ser Asp Leu Glu Asn Ala Thr Asp
                85                  90                  95

His Glu Gln Thr Leu Asn Ser Thr Glu Phe Lys Lys Thr Tyr Ser Asn
            100                 105                 110

Thr Thr Thr Thr Ser Thr Glu Asn Gly Phe Met Ile Gly Gln Glu Thr
        115                 120                 125

Glu Gly Lys Val Gly Ile Pro Phe Val Ala Glu Gly Lys Val Thr Ile
    130                 135                 140

Lys Thr Glu Tyr Asn Phe Asn His Thr Asn Gly Tyr Glu Thr Ser Glu
145                 150                 155                 160

Ser Val Glu Tyr Ile Ala Pro Ser Gln Ser Ile Lys Val Pro Pro His
                165                 170                 175

Thr Ile Ala Arg Val Thr Ala Leu Leu Asp Val Lys Lys Ile Lys Gly
            180                 185                 190

Lys Met His Leu Tyr Ser Glu Ile Gly Leu Asn Lys Asp Tyr Gly Tyr
        195                 200                 205

Asp Met Val Pro Leu Val Tyr Lys Tyr Gly Gly Pro Phe Lys Tyr Val
    210                 215                 220

Thr Leu Gly Thr Leu Tyr Asp Glu Gly Tyr Lys Gln Ala Gln Leu Asp
225                 230                 235                 240

Tyr Phe Asn Met Gly Asn Val Ile Pro Glu Ile Glu Thr Val Ser
                245                 250                 255

Lys Ser Asn Asn Pro Asn His Leu Leu Ala Ser Gly Val Gly Ile Phe
            260                 265                 270

Glu Ser Glu Tyr Gly Ser Val Phe Asn Val Lys Val Glu Tyr Ile Asn
        275                 280                 285
```

```
Ile Asn Thr Lys Lys Ile Glu Lys Thr Glu Asn Leu Thr Ile Glu Pro
    290                 295                 300

Thr Ile Val Pro Val Lys Gln Thr Asn Thr Lys
305                 310                 315

<210> SEQ ID NO 18
<211> LENGTH: 257
<212> TYPE: PRT
<213> ORGANISM: Bacillus thuringiensis

<400> SEQUENCE: 18

Met Arg Tyr Phe Leu Glu Val Lys Asn Ser Tyr Gly Gln Leu Ala Met
1               5                   10                  15

Glu Pro Gln Val Ile Ser Thr Thr Pro Leu Trp Ala Gly Gln Ser Asp
            20                  25                  30

Leu Glu Asn Ala Thr Asp His Glu Gln Thr Leu Asn Ser Thr Glu Phe
        35                  40                  45

Lys Lys Thr Tyr Ser Asn Thr Thr Thr Thr Ser Thr Glu Asn Gly Phe
    50                  55                  60

Met Ile Gly Gln Glu Thr Glu Gly Lys Val Gly Ile Pro Phe Val Ala
65                  70                  75                  80

Glu Gly Lys Val Thr Ile Lys Thr Glu Tyr Asn Phe Asn His Thr Asn
                85                  90                  95

Gly Tyr Glu Thr Ser Glu Ser Val Glu Tyr Ile Ala Pro Ser Gln Ser
            100                 105                 110

Ile Lys Val Pro Pro His Thr Ile Ala Arg Val Thr Ala Leu Leu Asp
        115                 120                 125

Val Lys Lys Ile Lys Gly Lys Met His Leu Tyr Ser Glu Ile Gly Leu
    130                 135                 140

Asn Lys Asp Tyr Gly Tyr Asp Met Val Pro Leu Val Tyr Lys Tyr Gly
145                 150                 155                 160

Gly Pro Phe Lys Tyr Val Thr Leu Gly Thr Leu Tyr Asp Glu Gly Tyr
                165                 170                 175

Lys Gln Ala Gln Leu Asp Tyr Phe Asn Met Gly Asn Val Ile Pro Glu
            180                 185                 190

Glu Ile Glu Thr Val Ser Lys Ser Asn Asn Pro Asn His Leu Leu Ala
        195                 200                 205

Ser Gly Val Gly Ile Phe Glu Ser Glu Tyr Gly Ser Val Phe Asn Val
    210                 215                 220

Lys Val Glu Tyr Ile Asn Ile Asn Thr Lys Lys Ile Glu Lys Thr Glu
225                 230                 235                 240

Asn Leu Thr Ile Glu Pro Thr Ile Val Pro Val Lys Gln Thr Asn Thr
                245                 250                 255

Lys

<210> SEQ ID NO 19
<211> LENGTH: 242
<212> TYPE: PRT
<213> ORGANISM: Bacillus thuringiensis

<400> SEQUENCE: 19

Met Glu Pro Gln Val Ile Ser Thr Thr Pro Leu Trp Ala Gly Gln Ser
1               5                   10                  15

Asp Leu Glu Asn Ala Thr Asp His Glu Gln Thr Leu Asn Ser Thr Glu
            20                  25                  30
```

```
Phe Lys Lys Thr Tyr Ser Asn Thr Thr Thr Ser Thr Glu Asn Gly
             35                  40                  45

Phe Met Ile Gly Gln Glu Thr Glu Gly Lys Val Gly Ile Pro Phe Val
 50                  55                  60

Ala Glu Gly Lys Val Thr Ile Lys Thr Glu Tyr Asn Phe Asn His Thr
 65                  70                  75                  80

Asn Gly Tyr Glu Thr Ser Glu Ser Val Glu Tyr Ile Ala Pro Ser Gln
                 85                  90                  95

Ser Ile Lys Val Pro Pro His Thr Ile Ala Arg Val Thr Ala Leu Leu
            100                 105                 110

Asp Val Lys Lys Ile Lys Gly Lys Met His Leu Tyr Ser Glu Ile Gly
            115                 120                 125

Leu Asn Lys Asp Tyr Gly Tyr Asp Met Val Pro Leu Val Tyr Lys Tyr
130                 135                 140

Gly Gly Pro Phe Lys Tyr Val Thr Leu Gly Thr Leu Tyr Asp Glu Gly
145                 150                 155                 160

Tyr Lys Gln Ala Gln Leu Asp Tyr Phe Asn Met Gly Asn Val Ile Pro
                165                 170                 175

Glu Glu Ile Glu Thr Val Ser Lys Ser Asn Asn Pro Asn His Leu Leu
            180                 185                 190

Ala Ser Gly Val Gly Ile Phe Glu Ser Glu Tyr Gly Ser Val Phe Asn
            195                 200                 205

Val Lys Val Glu Tyr Ile Asn Ile Asn Thr Lys Lys Ile Glu Lys Thr
            210                 215                 220

Glu Asn Leu Thr Ile Glu Pro Thr Ile Val Pro Val Lys Gln Thr Asn
225                 230                 235                 240

Thr Lys

<210> SEQ ID NO 20
<211> LENGTH: 343
<212> TYPE: PRT
<213> ORGANISM: Bacillus thuringiensis

<400> SEQUENCE: 20

Met Arg Glu Lys Asp Met Asp Lys Lys Ile Thr Lys Ala Ala Leu Ser
 1               5                  10                  15

Met Ile Met Gly Ile Ser Val Leu Ser Ser Pro Leu Ala Val Ala Ala
                 20                  25                  30

Lys Thr Glu Asn Asn Lys Glu Gln His Val Ile Thr Gln Phe Asn Gln
             35                  40                  45

Arg Glu Asn Lys Phe Pro Asp Val Gly Gln Gly Ile Gln Trp Leu Ser
 50                  55                  60

Gln Phe Tyr Gly Lys Ser Leu Lys Asn Asn Gly Glu Gly Tyr Ser Leu
 65                  70                  75                  80

Gly Gln Asp Val Met Ser Tyr Phe Leu Glu Val Lys Asn Ser Tyr Gly
                 85                  90                  95

Gln Leu Ala Met Glu Pro Gln Val Ile Ser Thr Thr Pro Leu Trp Ala
            100                 105                 110

Gly Gln Ser Asp Leu Glu Asn Ala Thr Asp His Glu Gln Thr Leu Asn
            115                 120                 125

Ser Thr Glu Phe Lys Lys Thr Tyr Ser Asn Thr Thr Thr Ser Thr
130                 135                 140

Glu Asn Gly Phe Met Ile Gly Gln Glu Thr Glu Gly Lys Val Gly Ile
145                 150                 155                 160
```

```
Pro Phe Val Ala Glu Gly Lys Val Thr Ile Lys Thr Glu Tyr Asn Phe
                165                 170                 175

Asn His Thr Asn Gly Tyr Glu Thr Ser Glu Ser Val Glu Tyr Ile Ala
            180                 185                 190

Pro Ser Gln Ser Ile Lys Val Pro Pro His Thr Ile Ala Arg Val Thr
        195                 200                 205

Ala Leu Leu Asp Val Lys Lys Ile Lys Gly Lys Met His Leu Tyr Ser
210                 215                 220

Glu Ile Gly Leu Asn Lys Asp Tyr Gly Tyr Asp Met Val Pro Leu Val
225                 230                 235                 240

Tyr Lys Tyr Gly Gly Pro Phe Lys Tyr Val Thr Leu Gly Thr Leu Tyr
                245                 250                 255

Asp Glu Gly Tyr Lys Gln Ala Gln Leu Asp Tyr Phe Asn Met Gly Asn
            260                 265                 270

Val Ile Pro Glu Glu Ile Glu Thr Val Ser Lys Ser Asn Asn Pro Asn
        275                 280                 285

His Leu Leu Ala Ser Gly Val Gly Ile Phe Glu Ser Gly Tyr Gly Ser
290                 295                 300

Val Phe Asn Val Lys Val Glu Tyr Ile Asn Ile Asn Thr Lys Lys Ile
305                 310                 315                 320

Glu Lys Thr Glu Asn Leu Thr Ile Glu Pro Thr Ile Val Pro Val Lys
                325                 330                 335

Gln Thr Asn Thr Asn Thr Lys
            340

<210> SEQ ID NO 21
<211> LENGTH: 338
<212> TYPE: PRT
<213> ORGANISM: Bacillus thuringiensis

<400> SEQUENCE: 21

Met Asp Lys Lys Ile Thr Lys Ala Ala Leu Ser Met Ile Met Gly Ile
1               5                   10                  15

Ser Val Leu Ser Ser Pro Leu Ala Val Ala Ala Lys Thr Glu Asn Asn
            20                  25                  30

Lys Glu Gln His Val Ile Thr Gln Phe Asn Gln Arg Glu Asn Lys Phe
        35                  40                  45

Pro Asp Val Gly Gln Gly Ile Gln Trp Leu Ser Gln Phe Tyr Gly Lys
    50                  55                  60

Ser Leu Lys Asn Asn Gly Glu Gly Tyr Ser Leu Gly Gln Asp Val Met
65                  70                  75                  80

Ser Tyr Phe Leu Glu Val Lys Asn Ser Tyr Gly Gln Leu Ala Met Glu
                85                  90                  95

Pro Gln Val Ile Ser Thr Thr Pro Leu Trp Ala Gly Ser Asp Leu
            100                 105                 110

Glu Asn Ala Thr Asp His Glu Gln Thr Leu Asn Ser Thr Glu Phe Lys
        115                 120                 125

Lys Thr Tyr Ser Asn Thr Thr Thr Ser Thr Glu Asn Gly Phe Met
    130                 135                 140

Ile Gly Gln Glu Thr Glu Gly Lys Val Gly Ile Pro Phe Val Ala Glu
145                 150                 155                 160

Gly Lys Val Thr Ile Lys Thr Glu Tyr Asn Phe Asn His Thr Asn Gly
                165                 170                 175

Tyr Glu Thr Ser Glu Ser Val Glu Tyr Ile Ala Pro Ser Gln Ser Ile
            180                 185                 190
```

```
Lys Val Pro Pro His Thr Ile Ala Arg Val Thr Ala Leu Leu Asp Val
            195                 200                 205

Lys Lys Ile Lys Gly Lys Met His Leu Tyr Ser Glu Ile Gly Leu Asn
210                 215                 220

Lys Asp Tyr Gly Tyr Asp Met Val Pro Leu Val Tyr Lys Tyr Gly Gly
225                 230                 235                 240

Pro Phe Lys Tyr Val Thr Leu Gly Thr Leu Tyr Asp Glu Gly Tyr Lys
                245                 250                 255

Gln Ala Gln Leu Asp Tyr Phe Asn Met Gly Asn Val Ile Pro Glu Glu
            260                 265                 270

Ile Glu Thr Val Ser Lys Ser Asn Pro Asn His Leu Leu Ala Ser
        275                 280                 285

Gly Val Gly Ile Phe Glu Ser Glu Tyr Gly Ser Val Phe Asn Val Lys
290                 295                 300

Val Glu Tyr Ile Asn Ile Asn Thr Lys Lys Ile Glu Lys Thr Glu Asn
305                 310                 315                 320

Leu Thr Ile Glu Pro Thr Ile Val Pro Val Lys Gln Thr Asn Thr Asn
                325                 330                 335

Thr Lys

<210> SEQ ID NO 22
<211> LENGTH: 327
<212> TYPE: PRT
<213> ORGANISM: Bacillus thuringiensis

<400> SEQUENCE: 22

Met Ile Met Gly Ile Ser Val Le

```
Tyr Lys Tyr Gly Gly Pro Phe Lys Tyr Val Thr Leu Gly Thr Leu Tyr
225                 230                 235                 240

Asp Glu Gly Tyr Lys Gln Ala Gln Leu Asp Tyr Phe Asn Met Gly Asn
                245                 250                 255

Val Ile Pro Glu Glu Ile Glu Thr Val Ser Lys Ser Asn Asn Pro Asn
            260                 265                 270

His Leu Leu Ala Ser Gly Val Gly Ile Phe Glu Ser Glu Tyr Gly Ser
        275                 280                 285

Val Phe Asn Val Lys Val Glu Tyr Ile Asn Ile Asn Thr Lys Lys Ile
    290                 295                 300

Glu Lys Thr Glu Asn Leu Thr Ile Glu Pro Thr Ile Val Pro Val Lys
305                 310                 315                 320

Gln Thr Asn Thr Asn Thr Lys
                325

<210> SEQ ID NO 23
<211> LENGTH: 325
<212> TYPE: PRT
<213> ORGANISM: Bacillus thuringiensis

<400> SEQUENCE: 23

Met Gly Ile Ser Val Leu Ser Ser Pro Leu Ala Val Ala Ala Lys Thr
1               5                   10                  15

Glu Asn Asn Lys Glu Gln His Val Ile Thr Gln Phe Asn Gln Arg Glu
            20                  25                  30

Asn Lys Phe Pro Asp Val Gly Gln Gly Ile Gln Trp Leu Ser Gln Phe
        35                  40                  45

Tyr Gly Lys Ser Leu Lys Asn Asn Gly Glu Gly Tyr Ser Leu Gly Gln
    50                  55                  60

Asp Val Met Ser Tyr Phe Leu Glu Val Lys Asn Ser Tyr Gly Gln Leu
65                  70                  75                  80

Ala Met Glu Pro Gln Val Ile Ser Thr Thr Pro Leu Trp Ala Gly Gln
                85                  90                  95

Ser Asp Leu Glu Asn Ala Thr Asp His Glu Gln Thr Leu Asn Ser Thr
            100                 105                 110

Glu Phe Lys Lys Thr Tyr Ser Asn Thr Thr Thr Thr Ser Thr Glu Asn
        115                 120                 125

Gly Phe Met Ile Gly Gln Glu Thr Glu Gly Lys Val Gly Ile Pro Phe
    130                 135                 140

Val Ala Glu Gly Lys Val Thr Ile Lys Thr Glu Tyr Asn Phe Asn His
145                 150                 155                 160

Thr Asn Gly Tyr Glu Thr Ser Glu Ser Val Glu Tyr Ile Ala Pro Ser
                165                 170                 175

Gln Ser Ile Lys Val Pro Pro His Thr Ile Ala Arg Val Thr Ala Leu
            180                 185                 190

Leu Asp Val Lys Lys Ile Lys Gly Lys Met His Leu Tyr Ser Glu Ile
        195                 200                 205

Gly Leu Asn Lys Asp Tyr Gly Tyr Asp Met Val Pro Leu Val Tyr Lys
    210                 215                 220

Tyr Gly Gly Pro Phe Lys Tyr Val Thr Leu Gly Thr Leu Tyr Asp Glu
225                 230                 235                 240

Gly Tyr Lys Gln Ala Gln Leu Asp Tyr Phe Asn Met Gly Asn Val Ile
                245                 250                 255

Pro Glu Glu Ile Glu Thr Val Ser Lys Ser Asn Asn Pro Asn His Leu
```

260                 265                 270

Leu Ala Ser Gly Val Gly Ile Phe Glu Ser Glu Tyr Gly Ser Val Phe
                275                 280                 285

Asn Val Lys Val Glu Tyr Ile Asn Ile Asn Thr Lys Lys Ile Glu Lys
            290                 295                 300

Thr Glu Asn Leu Thr Ile Glu Pro Thr Ile Val Pro Val Lys Gln Thr
305                 310                 315                 320

Asn Thr Asn Thr Lys
                325

<210> SEQ ID NO 24
<211> LENGTH: 259
<212> TYPE: PRT
<213> ORGANISM: Bacillus thuringiensis

<400> SEQUENCE: 24

Met Ser Tyr Phe Leu Glu Val Lys Asn Ser Tyr Gly Gln Leu Ala Met
1               5                   10                  15

Glu Pro Gln Val Ile Ser Thr Thr Pro Leu Trp Ala Gly Gln Ser Asp
            20                  25                  30

Leu Glu Asn Ala Thr Asp His Glu Gln Thr Leu Asn Ser Thr Glu Phe
        35                  40                  45

Lys Lys Thr Tyr Ser Asn Thr Thr Thr Ser Thr Glu Asn Gly Phe
    50                  55                  60

Met Ile Gly Gln Glu Thr Gly Lys Val Gly Ile Pro Phe Val Ala
65                  70                  75                  80

Glu Gly Lys Val Thr Ile Lys Thr Glu Tyr Asn Phe Asn His Thr Asn
                85                  90                  95

Gly Tyr Glu Thr Ser Glu Ser Val Glu Tyr Ile Ala Pro Ser Gln Ser
            100                 105                 110

Ile Lys Val Pro Pro His Thr Ile Ala Arg Val Thr Ala Leu Leu Asp
        115                 120                 125

Val Lys Lys Ile Lys Gly Lys Met His Leu Tyr Ser Glu Ile Gly Leu
130                 135                 140

Asn Lys Asp Tyr Gly Tyr Asp Met Val Pro Leu Val Tyr Lys Tyr Gly
145                 150                 155                 160

Gly Pro Phe Lys Tyr Val Thr Leu Gly Thr Leu Tyr Asp Glu Gly Tyr
                165                 170                 175

Lys Gln Ala Gln Leu Asp Tyr Phe Asn Met Gly Asn Val Ile Pro Glu
            180                 185                 190

Glu Ile Glu Thr Val Ser Lys Ser Asn Asn Pro Asn His Leu Leu Ala
        195                 200                 205

Ser Gly Val Gly Ile Phe Glu Ser Glu Tyr Gly Ser Val Phe Asn Val
    210                 215                 220

Lys Val Glu Tyr Ile Asn Ile Asn Thr Lys Lys Ile Glu Lys Thr Glu
225                 230                 235                 240

Asn Leu Thr Ile Glu Pro Thr Ile Val Pro Val Lys Gln Thr Asn Thr
                245                 250                 255

Asn Thr Lys

<210> SEQ ID NO 25
    <211> LENGTH: 244
<212> TYPE: PRT
<213> ORGANISM: Bacillus thuringiensis

<400> SEQUENCE: 25

```
Met Glu Pro Gln Val Ile Ser Thr Thr Pro Leu Trp Ala Gly Gln Ser
1               5                   10                  15

Asp Leu Glu Asn Ala Thr Asp His Glu Gln Thr Leu Asn Ser Thr Glu
            20                  25                  30

Phe Lys Lys Thr Tyr Ser Asn Thr Thr Thr Ser Thr Glu Asn Gly
        35                  40                  45

Phe Met Ile Gly Gln Glu Thr Glu Gly Lys Val Gly Ile Pro Phe Val
50                  55                  60

Ala Glu Gly Lys Val Thr Ile Lys Thr Glu Tyr Asn Phe Asn His Thr
65                  70                  75                  80

Asn Gly Tyr Glu Thr Ser Glu Ser Val Glu Tyr Ile Ala Pro Ser Gln
            85                  90                  95

Ser Ile Lys Val Pro Pro His Thr Ile Ala Arg Val Thr Ala Leu Leu
            100                 105                 110

Asp Val Lys Lys Ile Lys Gly Lys Met His Leu Tyr Ser Glu Ile Gly
            115                 120                 125

Leu Asn Lys Asp Tyr Gly Tyr Asp Met Val Pro Leu Val Tyr Lys Tyr
130                 135                 140

Gly Gly Pro Phe Lys Tyr Val Thr Leu Gly Thr Leu Tyr Asp Glu Gly
145                 150                 155                 160

Tyr Lys Gln Ala Gln Leu Asp Tyr Phe Asn Met Gly Asn Val Ile Pro
                165                 170                 175

Glu Glu Ile Glu Thr Val Ser Lys Ser Asn Asn Pro Asn His Leu Leu
            180                 185                 190

Ala Ser Gly Val Gly Ile Phe Glu Ser Glu Tyr Gly Ser Val Phe Asn
            195                 200                 205

Val Lys Val Glu Tyr Ile Asn Ile Asn Thr Lys Lys Ile Glu Lys Thr
210                 215                 220

Glu Asn Leu Thr Ile Glu Pro Thr Ile Val Pro Val Lys Gln Thr Asn
225                 230                 235                 240

Thr Asn Thr Lys

<210> SEQ ID NO 26
<211> LENGTH: 312
<212> TYPE: PRT
<213> ORGANISM: Bacillus thuringiensis

<400> SEQUENCE: 26

Met Lys Thr Glu Asn Asn Lys Glu Gln His Val Ile Thr Gln Phe Asn
1               5                   10                  15

Gln Arg Glu Asn Lys Phe Pro Asp Val Gly Gln Gly Ile Gln Trp Leu
            20                  25                  30

Ser Gln Phe Tyr Gly Lys Ser Leu Lys Asn Asn Gly Glu Gly Tyr Ser
        35                  40                  45

Leu Gly Gln Asp Val Met Ser Tyr Phe Leu Val Lys Asn Ser Tyr
50                  55                  60

Gly Gln Leu Ala Met Glu Pro Gln Val Ile Ser Thr Thr Pro Leu Trp
65                  70                  75                  80

Ala Gly Gln Ser Asp Leu Glu Asn Ala Thr Asp His Glu Gln Thr Leu
                85                  90                  95

Asn Ser Thr Glu Phe Lys Lys Thr Tyr Ser Asn Thr Thr Thr Thr Ser
            100                 105                 110

Thr Glu Asn Gly Phe Met Ile Gly Gln Glu Thr Glu Gly Lys Val Gly
            115                 120                 125
```

-continued

```
Ile Pro Phe Val Ala Glu Gly Lys Val Thr Ile Lys Thr Glu Tyr Asn
    130                 135                 140

Phe Asn His Thr Asn Gly Tyr Glu Thr Ser Glu Ser Val Glu Tyr Ile
145                 150                 155                 160

Ala Pro Ser Gln Ser Ile Lys Val Pro Pro His Thr Ile Ala Arg Val
                165                 170                 175

Thr Ala Leu Leu Asp Val Lys Lys Ile Lys Gly Lys Met His Leu Tyr
            180                 185                 190

Ser Glu Ile Gly Leu Asn Lys Asp Tyr Gly Tyr Asp Met Val Pro Leu
        195                 200                 205

Val Tyr Lys Tyr Gly Gly Pro Phe Lys Tyr Val Thr Leu Gly Thr Leu
    210                 215                 220

Tyr Asp Glu Gly Tyr Lys Gln Ala Gln Leu Asp Tyr Phe Asn Met Gly
225                 230                 235                 240

Asn Val Ile Pro Glu Glu Ile Glu Thr Val Ser Lys Ser Asn Asn Pro
                245                 250                 255

Asn His Leu Leu Ala Ser Gly Val Gly Ile Phe Glu Ser Glu Tyr Gly
            260                 265                 270

Ser Val Phe Asn Val Lys Val Glu Tyr Ile Asn Ile Asn Thr Lys Lys
        275                 280                 285

Ile Glu Lys Thr Glu Asn Leu Thr Ile Glu Pro Thr Ile Val Pro Val
    290                 295                 300

Lys Gln Thr Asn Thr Asn Thr Lys
305                 310

<210> SEQ ID NO 27
<211> LENGTH: 4
<212> TYPE: PRT
<213> ORGANISM: Artificial Sequence
<220> FEATURE:
<223> OTHER INFORMATION: Endoplasmic reticulum targeting peptide

<400> SEQUENCE: 27

Lys Asp Glu Leu
1
```